United States Patent
Khanna et al.

(10) Patent No.: US 10,287,334 B2
(45) Date of Patent: May 14, 2019

(54) NON-NARCOTIC CRMP2 PEPTIDES TARGETING SODIUM CHANNELS FOR CHRONIC PAIN

(71) Applicant: THE ARIZONA BOARD OF REGENTS ON BEHALF OF THE UNIVERSITY OF ARIZONA, Tucson, AZ (US)

(72) Inventors: Rajesh Khanna, Tucson, AZ (US); May Khanna, Tucson, AZ (US); Todd W. Vanderah, Tucson, AZ (US); Erik T. Dustrude, Tucson, AZ (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 59 days.

(21) Appl. No.: 15/124,304

(22) PCT Filed: Mar. 6, 2015

(86) PCT No.: PCT/US2015/019275
§ 371 (c)(1),
(2) Date: Sep. 7, 2016

(87) PCT Pub. No.: WO2015/134920
PCT Pub. Date: Sep. 11, 2015

(65) Prior Publication Data
US 2017/0008939 A1  Jan. 12, 2017

Related U.S. Application Data

(60) Provisional application No. 61/949,456, filed on Mar. 7, 2014.

(51) Int. Cl.
| | |
|---|---|
| A61K 38/10 | (2006.01) |
| A61K 38/16 | (2006.01) |
| C07K 14/00 | (2006.01) |
| C07K 19/00 | (2006.01) |
| C07K 14/47 | (2006.01) |
| C07K 5/09 | (2006.01) |
| C07K 7/06 | (2006.01) |
| C07K 7/08 | (2006.01) |
| A61K 38/00 | (2006.01) |

(52) U.S. Cl.
CPC .......... *C07K 14/47* (2013.01); *C07K 5/0815* (2013.01); *C07K 7/06* (2013.01); *C07K 7/08* (2013.01); *A61K 38/00* (2013.01)

(58) Field of Classification Search
None
See application file for complete search history.

(56) References Cited

U.S. PATENT DOCUMENTS

2003/0170826 A1   9/2003  Rabinovich et al.

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Anitua, E, et al. "Intranasal Delivery of Plasma and Platelet Growth Factors Using PRGF-Endoret System Enhances Neurogenesis in a Mouse Model of Alzheimer's Disease" PloS one 8, e73118 (2013).
Chaplan et al., "Quantitative assessment of tactile allodynia in the rat paw." J.Neurosci.Methods. 53, 55-63 (1994).
Dustrude et al. "CRMP2 protein SUMOylation modulates NaV1.7 channel trafficking." J. Biol. Chem. Aug. 23, 2013, vol. 288, No. 34, pp. 24316-24331.
Fischer, G., et al. "Sustained relief of neuropathic pain by AAV-targeted expression of CBD3 peptide in rat dorsal root ganglion." Gene therapy, 2014, 21, 44-51.
International Search Report, International Patent Application No. PCT/US2015/019275, dated Jun. 17, 2015.
Largent-Milnes, T.M., et al. "Spinal or systemic TY005, a peptidic opioid agonist/neurokinin 1 antagonist, attenuates pain with reduced tolerance" British Journal of Pharmacology 161, 986-1001 (2010).
Dustrude et al. "A Single Structurally Conserved SUMOylation Site in CRMP2 Controls NAV1.7 Function", Channels, 2017, pp. 1-13.
Ju, W. et al. "SUMOylation Alters CRMP2 Regulation of Calcium Influx in Sensory Neurons" Channels, 2013, vol. 7(3), pp. 153-159.
Arimura, N. et al. "Phosphorylation of Collapsin Response Mediator Protein-2 by Rho-kinase" The Journal of Biological Chemistry, 2000, vol. 275, No. 31, pp. 23973-23980.
Ju, W. et al. "Suppression of pain-related behavior in two distinct rodent models of peripheral neuropathy by a homopolyarginine-conjugated CRMP2 peptide." Journal of Nuerochemistry, 2013, 124, pp. 869-879.

* cited by examiner

*Primary Examiner* — Christine J Saoud
*Assistant Examiner* — Jon M Lockard
(74) *Attorney, Agent, or Firm* — Casimir Jones, S.C.

(57) ABSTRACT

Disclosed herein are isolated polypeptides capable of preventing collapsin response mediator protein 2 (CRMP2)-small ubiquitin-like modifier (SUMO)ylation mediated trafficking of voltage gated sodium channel 1.7 (Nav1.7) function. In some examples, the disclosed peptides comprise three to twenty amino acids and include the amino acid sequence KMD. Also disclosed are methods of decreasing nociception including administering an effective amount of one or more disclosed peptides to a subject in need thereof, such as a subject experiencing chronic pain.

10 Claims, 7 Drawing Sheets
Specification includes a Sequence Listing.

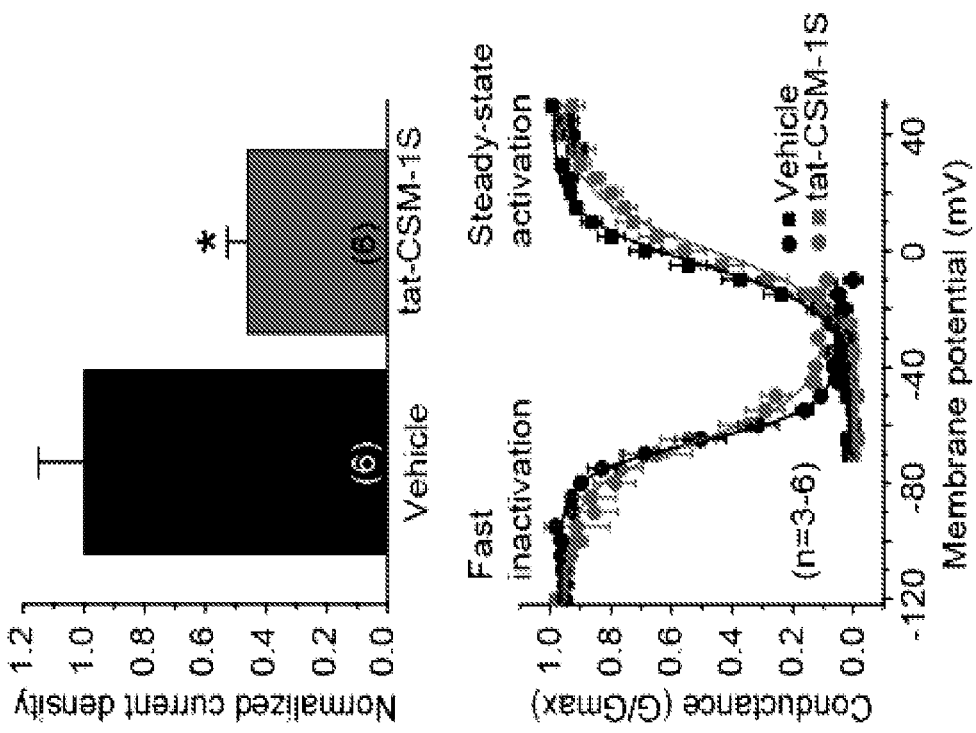
FIG. 4A
FIG. 4C
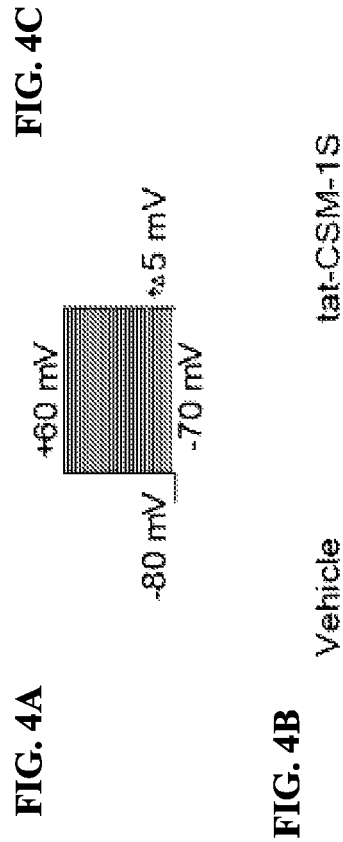
FIG. 4B
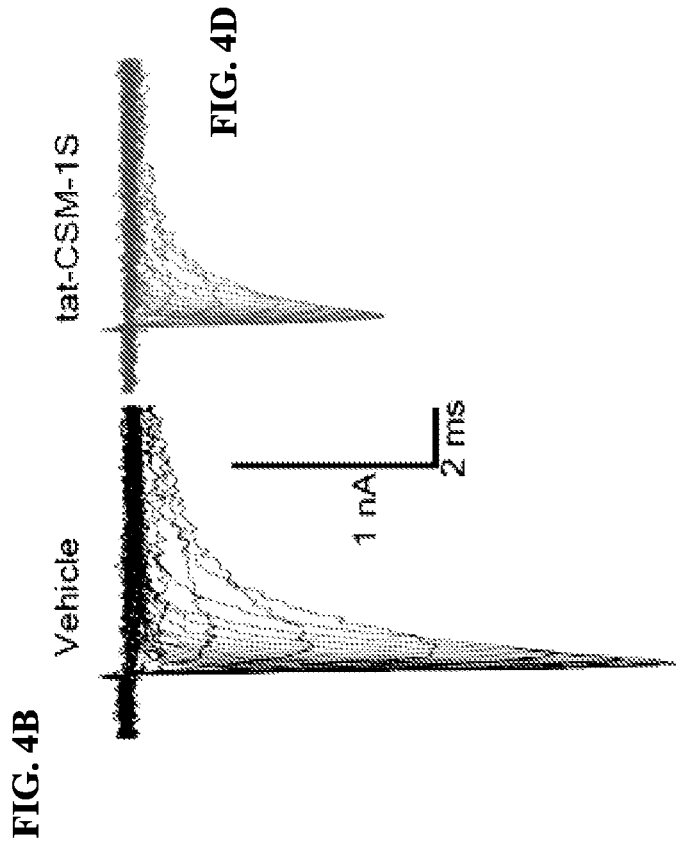
FIG. 4D

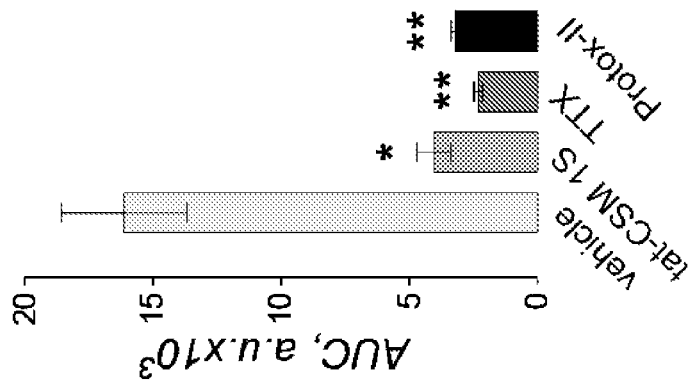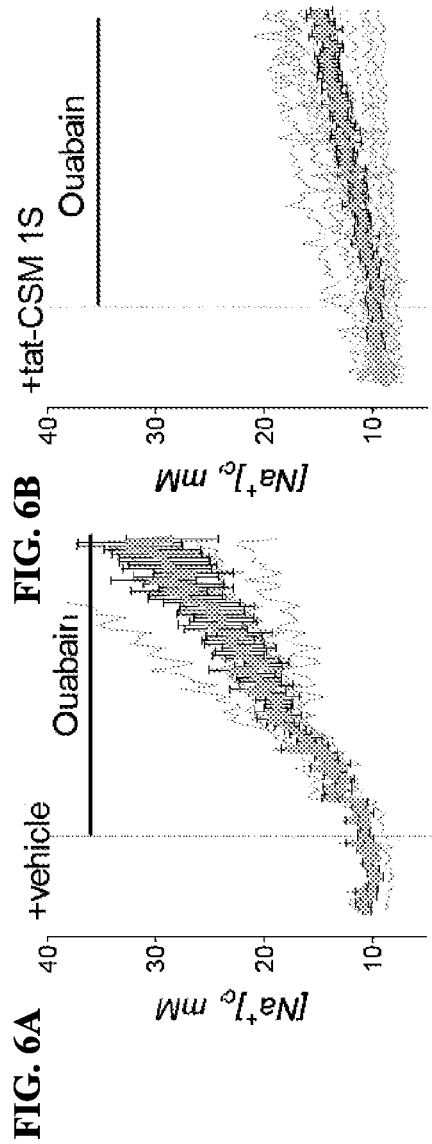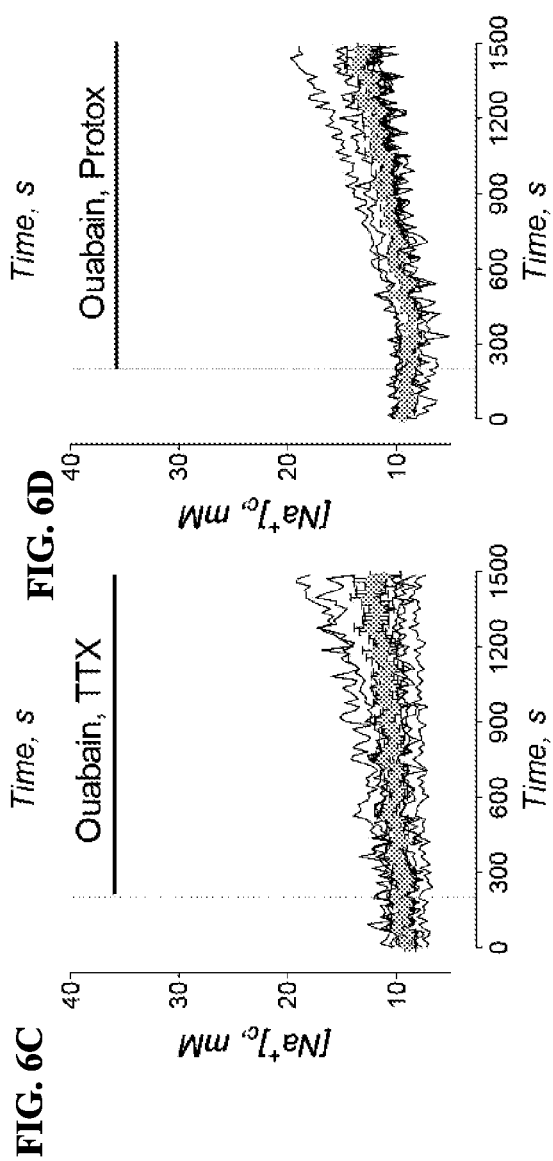

SEQUENCE LISTING

```
<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: synthetic peptide

<400> SEQUENCE: 1

Gly Lys Met Asp Glu Asn Gln
1               5

<210> SEQ ID NO 2
<211> LENGTH: 18
<212> TYPE: PRT
<213> ORGANISM: Artificial Sequence
<220> FEATURE:
<223> OTHER INFORMATION: synthetic peptide
```

```
<400> SEQUENCE: 2

Trp Asp Lys Ala Val Val Thr Gly Lys Met Asp Glu Asn Gln Phe Val
1               5                   10                  15

Ala Val

<210> SEQ ID NO 3
<211> LENGTH: 13
<212> TYPE: PRT
<213> ORGANISM: Artificial Sequence
<220> FEATURE:
<223> OTHER INFORMATION: Cell penetrating motif

<400> SEQUENCE: 3

Gly Arg Lys Lys Arg Arg Gln Arg Arg Pro Pro Gln
1               5                   10

<210> SEQ ID NO 4
<211> LENGTH: 16
<212> TYPE: PRT
<213> ORGANISM: Artificial Sequence
<220> FEATURE:
<223> OTHER INFORMATION: cell penetrating motif

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: cell penetrating motif

<400> SEQUENCE: 5

Leu Leu Ile Ile Leu Arg Arg Arg Ile Arg Lys Gln Ala His Ala His
1               5                   10                  15

Ser Lys

<210> SEQ ID NO 6
<211> LENGTH: 18
<212> TYPE: PRT
<213> ORGANISM: Artificial Sequence
<220> FEATURE:
<223> OTHER INFORMATION: cell penetrating motif

<400> SEQUENCE: 6

Arg Gly Gly Arg Leu Ser Tyr Ser Arg Arg Phe Ser Thr Ser Thr
1               5                   10                  15

Gly Arg

<210> SEQ ID NO 7
<211> LENGTH: 9
<212> TYPE: PRT
<213> ORGANISM: Artificial Sequence
<220> FEATURE:
<223> OTHER INFORMATION: cell penetrating motif

<400> SEQUENCE: 7

Arg Arg Arg Arg Arg Arg Arg Arg Arg
1               5
```

```
<210> SEQ ID NO 8
<211> LENGTH: 13
<212> TYPE: PRT
<213> ORGANISM: Artificial Sequence
<220> FEATURE:
<223> OTHER INFORMATION: cell penetrating motif

<400> SEQUENCE: 8

Gly Arg Arg Arg Arg Arg Arg Arg Arg Pro Pro Gln
1               5                   10

<210> SEQ ID NO 9
<211> LENGTH: 16
<212> TYPE: PRT
<213> ORGANISM: Artificial Sequence
<220> FEATURE:
<223> OTHER INFORMATION: cell penetrating motif

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 18
<212> TYPE: PRT
<213> ORGANISM: Artificial Sequence
<220> FEATURE:
<223> OTHER INFORMATION: cell penetrating motif

<400> SEQUENCE: 10

Lys Leu Ala Leu Lys Leu Ala Leu Lys Ala Leu Lys Ala Ala Leu Lys
1               5                   10                  15

Leu Ala

<210> SEQ ID NO 11
<211> LENGTH: 13
<212> TYPE: PRT
<213> ORGANISM: Artificial Sequence
<220> FEATURE:
<223> OTHER INFORMATION: cell penetrating motif

<400> SEQUENCE: 11

Thr Arg Arg Gln Arg Thr Arg Arg Ala Arg Arg Asn Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: cell penetrating motif

<400> SEQUENCE: 12

Pro Leu Ser Ser Ile Phe Ser Arg Ile Gly Asp Pro
1               5                   10

<210> SEQ ID NO 13
<211> LENGTH: 28
<212> TYPE: PRT
<213> ORGANISM: Artificial Sequence
<220> FEATURE:
<223> OTHER INFORMATION: cell penetrating motif
```

```
<400> SEQUENCE: 13

Met Ala Leu Asn Leu Gly Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 14
<211> LENGTH: 21
<212> TYPE: PRT
<213> ORGANISM: Artificial Sequence
<220> FEATURE:
<223> OTHER INFORMATION: cell penetrating motif

<400> SEQUENCE: 14

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 15
<211> LENGTH: 12
<212> TYPE: PRT
<213> ORGANISM: Artificial Sequence
<220> FEATURE:
<223> OTHER INFORMATION: cell penetrating motif

<400> SEQUENCE: 15

Pro Leu Ser Ser Ile Phe Ser Arg Ile Gly Asp Pro
1               5                   10

<210> SEQ ID NO 16
<211> LENGTH: 18
<212> TYPE: PRT
<213> ORGANISM: Artificial Sequence
<220> FEATURE:
<223> OTHER INFORMATION: modulatory motif

<400> SEQUENCE: 16

Trp Asp Lys Ala Val Ala Thr Gly Lys Met Asp Glu Asn Gln Phe Val
1               5                   10                  15

Ala Val

<210> SEQ ID NO 17
<211> LENGTH: 18
<212> TYPE: PRT
<213> ORGANISM: Artificial Sequence
<220> FEATURE:
<223> OTHER INFORMATION: modulatory motif

<400> SEQUENCE: 17

Trp Glu Lys Cys Val Ala Ser Gly Lys Met Asp Glu Asn Glu Phe Val
1               5                   10                  15

Ala Val

<210> SEQ ID NO 18
<211> LENGTH: 18
<212> TYPE: PRT
<213> ORGANISM: Artificial Sequence
<220> FEATURE:
<223> OTHER INFORMATION: modulatory motif
```

-continued

```
<400> SEQUENCE: 18

Trp Glu Lys Cys Val Ala Ser Gly Lys Met Asp Glu Asn Glu Phe Val
1               5                   10                  15

Ala Val

<210> SEQ ID NO 19
<211> LENGTH: 18
<212> TYPE: PRT
<213> ORGANISM: Artificial Sequence
<220> FEATURE:
<223> OTHER INFORMATION: modulatory motif

<400> SEQUENCE: 19

Trp Glu Arg Gly Val Gly Gly Lys Met Asp Glu Asn Arg Phe Val
1               5                   10                  15

Ala Val

<210> SEQ ID NO 20
<211> LENGTH: 572
<212> TYPE: PRT
<213> ORGANISM: Rattus norvegicus

<400> SEQUENCE: 20

Met Ser Tyr Gln Gly Lys Lys Asn Ile Pro Arg Ile Thr Ser Asp Arg
1               5                   10                  15

Leu Leu Ile Lys Gly Gly Lys Ile Val Asn Asp Asp Gln Ser Phe Tyr
                20                  25                  30

Ala Asp Ile Tyr Met Glu Asp Gly Leu Ile Lys Gln Ile Gly Glu Asn
            35                  40                  45

Leu Ile Val Pro Gly Gly Val Lys Thr Ile Glu Ala His Ser Arg Met
    50                  55                  60

Val Ile Pro Gly Gly Ile Asp Val His Thr Arg Phe Gln Met Pro Asp
65                  70                  75                  80

Gln Gly Met Thr Ser Ala Asp Asp Phe Phe Gln Gly Thr Lys Ala Ala
                85                  90                  95

Leu Ala Gly Gly Thr Thr Met Ile Ile Asp His Val Val Pro Glu Pro
            100                 105                 110

Gly Thr Ser Leu Leu Ala Ala Phe Asp Gln Trp Arg Glu Trp Ala Asp
        115                 120                 125

Ser Lys Ser Cys Cys Asp Tyr Ser Leu His Val Asp Ile Thr Glu Trp
    130                 135                 140

His Lys Gly Ile Gln Glu Glu Met Glu Ala Leu Val Lys Asp His Gly
145                 150                 155                 160

Val Asn Ser Phe Leu Val Tyr Met Ala Phe Lys Asp Arg Phe Gln Leu
                165                 170                 175

Thr Asp Ser Gln Ile Tyr Glu Val Leu Ser Val Ile Arg Asp Ile Gly
            180                 185                 190

Ala Ile Ala Gln Val His Ala Glu Asn Gly Asp Ile Ile Ala Glu Glu
        195                 200                 205

Gln Gln Arg Ile Leu Asp Leu Gly Ile Thr Gly Pro Glu Gly His Val
    210                 215                 220

Leu Ser Arg Pro Glu Glu Val Glu Ala Glu Ala Val Asn Arg Ser Ile
225                 230                 235                 240

Thr Ile Ala Asn Gln Thr Asn Cys Pro Leu Tyr Val Thr Lys Val Met
                245                 250                 255
```

```
Ser Lys Ser Ala Ala Glu Val Ile Ala Gln Ala Arg Lys Lys Gly Thr
            260                 265                 270

Val Val Tyr Gly Glu Pro Ile Thr Ala Ser Leu Gly Thr Asp Gly Ser
        275                 280                 285

His Tyr Trp Ser Lys Asn Trp Ala Lys Ala Ala Phe Val Thr Ser
290                 295                 300

Pro Pro Leu Ser Pro Asp Pro Thr Thr Pro Asp Phe Leu Asn Ser Leu
305                 310                 315                 320

Leu Ser Cys Gly Asp Leu Gln Val Thr Gly Ser Ala His Cys Thr Phe
                325                 330                 335

Asn Thr Ala Gln Lys Ala Val Gly Lys Asp Asn Phe Thr Leu Ile Pro
            340                 345                 350

Glu Gly Thr Asn Gly Thr Glu Glu Arg Met Ser Val Ile Trp Asp Lys
            355                 360                 365

Ala Val Val Thr Gly Lys Met Asp Glu Asn Gln Phe Val Ala Val Thr
        370                 375                 380

Ser Thr Asn Ala Ala Lys Val Phe Asn Leu Tyr Pro Arg Lys Gly Arg
385                 390                 395                 400

Ile Ser Val Gly Ser Asp Ala Asp Leu Val Ile Trp Asp Pro Asp Ser
                405                 410                 415

Val Lys Thr Ile Ser Ala Lys Thr His Asn Ser Ala Leu Glu Tyr Asn
            420                 425                 430

Ile Phe Glu Gly Met Glu Cys Arg Gly Ser Pro Leu Val Val Ile Ser
            435                 440                 445

Gln Gly Lys Ile Val Leu Glu Asp Gly Thr Leu His Val Thr Glu Gly
    450                 455                 460

Ser Gly Arg Tyr Ile Pro Arg Lys Pro Phe Pro Asp Phe Val Tyr Lys
465                 470                 475                 480

Arg Ile Lys Ala Arg Ser Arg Leu Ala Glu Leu Arg Gly Val Pro Arg
                485                 490                 495

Gly Leu Tyr Asp Gly Pro Val Cys Glu Val Ser Val Thr Pro Lys Thr
            500                 505                 510

Val Thr Pro Ala Ser Ser Ala Lys Thr Ser Pro Ala Lys Gln Gln Ala
        515                 520                 525

Pro Pro Val Arg Asn Leu His Gln Ser Gly Phe Ser Leu Ser Gly Ala
530                 535                 540

Gln Ile Asp Asp Asn Ile Pro Arg Arg Thr Thr Gln Arg Ile Val Ala
545                 550                 555                 560

Pro Pro Gly Gly Arg Ala Asn Ile Thr Ser Leu Gly
                565                 570
```

NON-NARCOTIC CRMP2 PEPTIDES TARGETING SODIUM CHANNELS FOR CHRONIC PAIN

CROSS REFERENCE TO RELATED APPLICATIONS

This application is a U.S. 371 national phase entry of International Patent Application No. PCT/US2015/019275, filed Mar. 6, 2015, which claims priority to and the benefit of U.S. Provisional Application No. 61/949,456, filed Mar. 7, 2014, which are hereby incorporated by reference in their entireties.

FIELD

This disclosure relates to peptides and in particular, to non-narcotic analgesic peptides and methods of use thereof, including for treating chronic pain.

BACKGROUND

Approximately 1.5 billion people worldwide suffer from chronic pain of various etiologies. Pain is a leading cause of combat injured soldiers' and veterans' disability. Acute and chronic pain afflicts military personnel and veterans in proportions far exceeding those of the general population. A limited cohort study of Operation Enduring Freedom or Operation Iraqi Freedom veterans found 81.5% experienced chronic pain. Almost 30% of all veterans seek healthcare treatment for persistent chronic pain.

Currently, opioids, such as morphine, are the cornerstone of pain management in veterans suffering from chronic pain due to severe injuries (polytrauma), post-traumatic stress disorder (PTSD) and traumatic brain injury (TBI) or post-concussive syndrome. However, therapeutic administration of morphine often does not result in adequate, long lasting attenuation of chronic pain, as well as produces a number of deleterious side effects including respiratory depression, sedation, constipation, nausea, vomiting, addiction, tolerance, and increased suicide risks. Prescribed opioids (e.g., µ-opioid receptor agonists) have become some of the most highly abused drugs as measured by treatment center admission/cause of overdose; abuse of prescription drugs by the military is more than twice that seen in the civilian population—11% compared to 5%, according to a 2008 military survey. Alternative non-opioid based pain therapies are urgently needed. A deeper understanding of the complexity of pain mechanisms will lead to more rational and targeted approaches to pain therapies and to safer and more effective pain treatments.

SUMMARY

Disclosed herein are peptides for regulating voltage gated sodium channels isoform 1.7 (Nav1.7). In particular, the disclosed peptides prevent, inhibit and/or reduce collapsin response mediator protein 2 (CRMP2)-small ubiquitin-like modifier (SUMO)ylation mediated trafficking of Nav1.7 function and can be used to modulate disorders, conditions and diseases regulated by Nav1.7, including the management of pain, such as chronic pain states (e.g., burn pain, arthritic pain, bowel inflammation, some cancer pains, and neuroinflammation that accompanies some kinds of nerve injury, such as diabetic neuropathy).

In some embodiments, disclosed is an isolated polypeptide consisting of three to twenty amino acids capable of preventing, inhibiting and/or reducing collapsin response mediator protein 2 (CRMP2)-small ubiquitin-like modifier (SUMO)ylation mediated trafficking of voltage gated sodium channel 1.7 (Nav1.7) function and wherein the three to twenty amino acids comprise the amino acid sequence KMD.

In some embodiments, the peptide comprises three to eight amino acids. In some embodiments, the peptide comprises an amino acid sequence with 95% sequence identity to the amino acid sequence GKMDENQ (designated CSM-1S; SEQ ID NO: 1). In some embodiments, the peptide comprises the amino acid sequence GKMDENQ (CSM-1S; SEQ ID NO: 1).

In some embodiments, the peptide comprises an amino acid sequence with 95% sequence identity to the amino acid sequence WDKAVVTGKMDENQFVAV (CSM-1L; SEQ ID NO: 2). In some embodiments, the peptide comprises the amino acid sequence WDKAVVTGKMDENQFVAV (designated CSM-1L; SEQ ID NO: 2). In some embodiments, the isolated peptide further comprises a cell penetrating motif, such as a cell penetrating motif with the amino acid sequence of:

(a) GRKKRRQRRRPPQ; (SEQ ID NO: 3)

(b) RQIKIWFQNRRMKWKK; (SEQ ID NO: 4)

(c) LLIILRRRIRKQAHAHSK; (SEQ ID NO: 5)

(d) RGGRLSYSRRRFSTSTGR; (SEQ ID NO: 6)

(e) RRRRRRRRR; (SEQ ID NO: 7)

(f) GRRRRRRRRPPQ; (SEQ ID NO: 8)

(g) AAVALLPAVLLALLAP; (SEQ ID NO: 9)

(h) KLALKLALKALKAALKLA; (SEQ ID NO: 10)

(i) TRRQRTRRARRNR; (SEQ ID NO: 11)

(j) PLSSIFSRIGDP; (SEQ ID NO: 12)

(k) MALNLGWLLALFVTMWTDVGLCKKRPKP; (SEQ ID NO: 13)

(l) AGYLLGKINLKALAALAKKIL; (SEQ ID NO: 14)

or (m) PLSSIFSRIGDP. (SEQ ID NO: 15)

Also provided are compositions comprising an isolated polypeptide and a pharmaceutically acceptable carrier. In some embodiments, a vector comprising a nucleic acid sequence encoding a disclosed polypeptide is provided. In some embodiments, a cell comprising a disclosed vector construct is provided.

Methods of decreasing nociception are provided. In some embodiments, the methods comprise administering to a subject an effective amount of a disclosed isolated polypeptide or composition, thereby decreasing nociception in the subject. In some examples, the peptide or composition is administered by intravenous, intrathecal, intraperitoneal, subcutaneous, oral, transdermal, epidural, or sublingual administration. In some examples, the subject is at risk or has acute pain, chronic pain, nociceptic pain, cancer pain, neuralgia pain, myalgia pain, burn pain, arthritic pain, bowel inflammation pain, bone and/or osteoporosis pain, inflammatory pain or a combination thereof. In some examples, the subject is at risk or has a neurological disorder, such as Parkinson's Disease, Alzheimer's Disease, Pick's Disease, and/or Chronic Fatigue Syndrome. In some examples, the subject is at risk or has an emotional and/or mood disorder, such as depression, PTSD, anxiety, addiction and obsessive compulsive disorder.

The foregoing and other features and advantages of the disclosure will become more apparent from the following detailed description, which proceeds with reference to the accompanying figures.

BRIEF DESCRIPTION OF THE DRAWINGS

(FIG. 1A) The reversible SUMO cycle and general consequences for a modified protein, such as CRMP2: (i) SUMOylation can interfere with the interaction between the target and its partner, in which case the interaction can only occur in the absence of SUMOylation. (ii) SUMOylation can provide a binding site for an interacting partner. (iii) SUMOylation can result in a conformational change of the modified target. Which of these scenarios occurs with CRMP2 is unknown. (FIG. 1B) Alignment of a short region of rodent CRMPs 1 to 5 sequences (SEQ ID NO: 16, SEQ ID NO: 2, SEQ ID NO: 17, SEQ ID NO: 18 and SEQ ID NO: 19, respectively) with the SUMOylation consensus motif of CRMPs highlighted in yellow. The presence of negatively-charged, acidic patch (to the right) flanking the canonical motif conforms to the more stringent NDSM. The numbers refer to the amino acid residues of rat CRMP2. (FIG. 1C) Structural representation of CRMP2 with SUMOylation motif residues identified by spheres (arrow). For clarity only three monomers of the CRMP2 tetramer are shown.

FIGS. 4A-4D A cell penetrant form of the CRMP2 SUMOylation motif (CSM) peptide inhibits Nav1.7 currents in sensory neurons. FIG. 4A. Voltage protocol. FIG. 4B. Representative family of current traces from vehicle- or tat-CSM-1S (20 μM)-treated DRG neurons demonstrating marked reduction in currents. FIG. 4C. Summary data of peak current density (pA/pF) from the two conditions. Asterisk represents significant decrease in Nav1.7 current density ($p<0.05$, Student's t-test). Numbers in parentheses represent numbers of cells tested. FIG. 4D. Representative Boltzmann fits for activation and steady-state inactivation for Nav currents from vehicle- or tat-CSM-1S-treated DRGs.

FIGS. 6A-6E. Peptide tat-CSM 15, tetrodotoxin (TTX), and Protox-II, a spider toxin that preferentially blocks NaV1.7, attenuate ouabain-induced increase in cytosolic $Na^+$ in rat dorsal root ganglion (DRG) neurons in culture. Acutely dissociated DRG neurons plated on glass coverslips were loaded with SBFI, a $Na^+$-sensitive fluorophore and then were treated with 1 mM ouabain alone (FIG. 6A) or in combination with 1 μM TTX (FIG. 6C) or 10 μM Protox (FIG. 6D), as indicated. In FIG. 6B, neurons were pre-incubated with 10 μM tat-CSM 1S for 12 hours, and then loaded with SBFI and taken into the study. In FIG. 6E, a statistical analysis of ouabain-induced changes in cytosolic $Na^+$ ($[Na^+]c$). The ouabain-induced changes in $[Na^+]c$ over time were quantified by calculating the area under the curve (AUC) as it has been done previously for calcium imaging experiments. In these studies, the AUC was calculated for 1200 seconds following application of ouabain and other drugs. Data are mean±SEM, *$p<0.05$, **$p<0.01$. N=3 independent studies (n=18-27 cells per study).

FIG. 7A) Anti-hyperalgesic effects of tat-CSM-1S in SNI and the analgesic effects in the sham animals. FIG. 7B) Antiallodynic effects of tat-CSM-1S in the SNI animals (*$p<0.05$, when compared to BL-Post SNI, n=6).

FIG. 8A) Anti-hyperalgesic effects of gabapentin or morphine in SNI. FIG. 8B) Antiallodynic effects of gabapentin or morphine in the SNI animals (*$p<0.05$, when compared to BL-Post SNI, n=7-8).

SEQUENCE LISTING

Figure 1C:
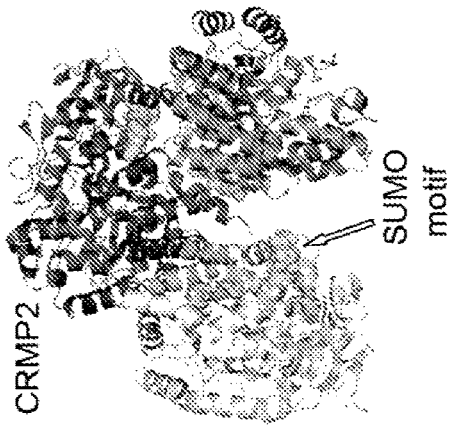
FIGS. 1A-1C. CRMP2 contains a conserved negatively-charged SUMOylation motif (NDSM) consensus sequence.

The nucleic and amino acid sequences listed in the sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is an amino acid sequence for exemplary peptide CSM-1S;

SEQ ID NO: 2 is a consensus amino acid sequence for exemplary peptide CSM-1L;

SEQ ID NOS: 3-15 are amino acid sequences for an exemplary cell penetrating motifs;

SEQ ID NO: 16 is a partial amino acid sequence from CRMP1;

SEQ ID NO: 17 is a partial amino acid sequence from CRMP3;

SEQ ID NO: 18 is a partial amino acid sequence from CRMP4;

SEQ ID NO: 19 is a partial amino acid sequence from CRMP5; and

SEQ ID NO: 20 is the complete amino acid sequence for rat CRMP2.

The Sequence Listing is submitted as an ASCII text file in the form of the file named Sequence.txt, which was created on Mar. 6, 2015, and is 9.96 kilobytes, which is incorporated by reference herein.

DETAILED DESCRIPTION

I. Introduction

Pain signaling typically originates in sensory neurons of the peripheral nervous system that relay information to the central nervous system (CNS). Pathological pain sensations can arise as a result of changes in excitability of these peripheral sensory neurons. Voltage-gated sodium channels (VGSCs, Nav) are key determinants regulating action potential generation and propagation; thus, changes in sodium channel function can have profound effects on neuronal excitability and pain signaling. The Nav1.7 isoform is preferentially expressed in the peripheral nervous system within ganglia related to nociceptive pain, including dorsal root ganglia, trigeminal ganglia and sympathetic ganglia. In nociceptive neurons responsible for the transduction of pain signals, the channel modulates current threshold required to fire action potentials in response to stimuli.

Nav1.7 is a target for regulating pain, since loss-of-function mutations in SCN9A, the gene that encodes Nav1.7, are associated with a syndrome of congenital insensitivity to pain, whereas gain-of-function mutations are linked to the debilitating chronic pain conditions erythromelalgia and paroxysmal extreme pain disorder. Upregulated expression of Nav 1.7 accompanies pain resulting from diabetic neuropathy, after peripheral inflammation induced by carrageenan or complete Freund's adjuvant (CFA), after combined sciatic nerve compression and nucleus pulposus application modeling lumbar disc herniation, and after spared nerve injury (SNI), Conversely, herpes vector-mediated knockdown of Nav 1.7 in dorsal root ganglion (DRG) sensory neurons significantly prevents the development of hyperalgesia in response to CFA. Nav1.7 knockout mice also fail to develop hyperalgesia in several inflammatory pain models.

Data from human and animal studies indicate a role for Nav 1.7 in nociception. Selective inhibitors of Nav1.7 are therefore likely to be powerful analgesics for treating a broad range of pain conditions. Development of Nav1.7-based analgesics has proven very difficult, as it is essential to avoid off-target effects on closely related Nav channels (e.g., Nav1.1 and Nav1.3) with critical physiological roles. An alternative approach, targeting regulators of Nav1.7 channels, may offer an advantage by targeting a regulatory checkpoint rather than the channel itself, and is disclosed herein.

The control of Nav channel density at the cell membrane is important to ensuring normal neuronal excitability. Despite extensive research on the subject, the regulation of Nav channels in neuropathic pain remains poorly understood. Post-translational regulation and direct, as well as indirect, protein-protein interactions have been advanced as possible regulatory mechanisms for Nav channel trafficking. The inventors have identified a novel regulatory mechanism that utilizes post-translational modification of collapsin response mediator protein 2 (CRMP2) to choreograph Nav1.7 trafficking.

Collapsin response mediator protein 2 (CRMP2) (GenBank Accession number NM_001386.5 (human), NP_001099187.1 (rat), and NP_034085.2 (mouse) each of which is incorporated by reference as of Mar. 7, 2014), also known as DPYSL2/DRP2, Unc-33, Ulip, or TUC2, specifies axon/dendrite fate and axonal outgrowth. Mapping the CRMP2 interactome has unraveled novel targets, which enable it to subserve roles in regulation of microtubule dynamics, protein endocytosis, vesicle recycling, and synaptic assembly within neurons. Trafficking of ligand- and voltage-gated calcium channels has been recently demonstrated as an additional role for CRMP2. The inventors have identified a novel post-translational modification of CRMP2 by addition of small ubiquitin-like modifier (SUMO).

Figure 1B:
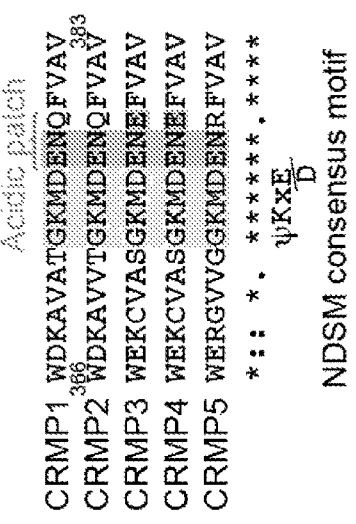
Figure 1A:
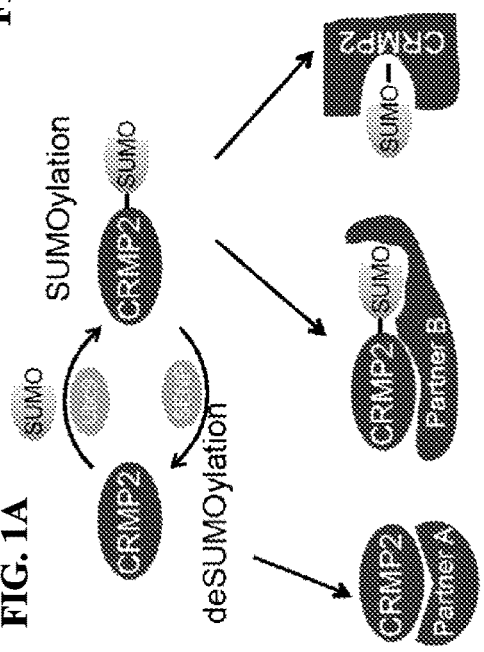

Modification by small ubiquitin-like modifier (SUMO), SUMOylation, is a covalent, reversible post-translational event that can add one of three ~11 kD SUMO proteins to lysines within target proteins (FIG. 1A). As with ubiquitination, a cascade of three enzymes, E1-activating, E2-conjugating and E3-ligase produce an isopeptide bond between the C-terminal glycine of SUMOs 1-3 and an ε-amino group of a target lysine within a SUMO motif on the acceptor protein. A typical motif is characterized by a large hydrophobic amino acid (ψ) preceding a target lysine followed by negatively charged amino acid two sites downstream (ψ-K-X-E/D). The E2 enzyme, Ubc9, may conjugate one or more of the three vertebrate SUMO proteins to a target lysine, while the sentrin/SUMO-specific protease (SENP) 1 and SENP2 removes SUMOs, thus reversing the modification. SUMOylation has been implicated in modulation of several ion channels and receptors, including inactivation of voltage-gated potassium channels Kv1.5, activation of Kv2.1 and endocytosis of glutamate receptor isoform 6 (GluR6). Glutamate receptor isoforms GluR7, and metabotropic GluRs (mGluRs) 2, 4, 6, 7a and 7b have also been shown to be targets of SUMOylation. CRMP2 has not been demonstrated to interact with any of these proteins.

The inventors demonstrated that destruction of the small ubiquitin-like modifier (SUMO) modification site in CRMP2 was sufficient to selectively decrease trafficking of Nav1.7, but not Nav1.1 or Nav1.3, channels. It is unknown whether Nav1.7 is itself the target of SUMOylation; however, of the TTX-sensitive voltage-gated sodium channels present in the nervous system, only Nav1.7 lacks a putative SUMOylation motif. Thus any effect on the channel by SUMOylation is likely to be due to indirect modification of accessory proteins, such as CRMP2 demonstrated in this study. Mechanisms that specifically or preferentially regulate Nav1.7 are of particular relevance due to the role of Nav1.7 upregulation and transduction of peripheral pain. Thus, development of a selective Nav1.7 channel trafficking blocker is highly desirable for the treatment of chronic pain states including burn pain, arthritic pain, bowel inflammation, some cancer pains, and neuroinflammation that accompanies some kinds of nerve injury, such as diabetic neuropathy.

Figure 2:
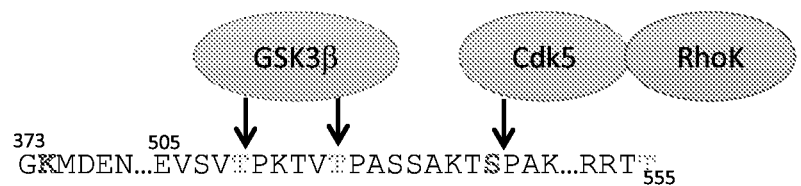
FIG. 2. CRMP2 sequence—sites of phosphorylation and SUMOylation. Sites of phosphorylation by glycogen 3 kinase beta (GSK3β), cyclin-dependent kinase 5 (Cdk5), and Rho kinase (RhoK), are illustrated in the partially shown rat CRMP2 sequence (see SEQ ID NO: 20 for complete sequence; GenBANK Accession no. P47942 which is hereby incorporated by reference in its entirety as available on Mar. 6, 2015). The small ubiquitin-like modifier (SUMO) ylated lysine at residue 374 of SEQ ID NO: 20 is also indicated.
Figure 3:
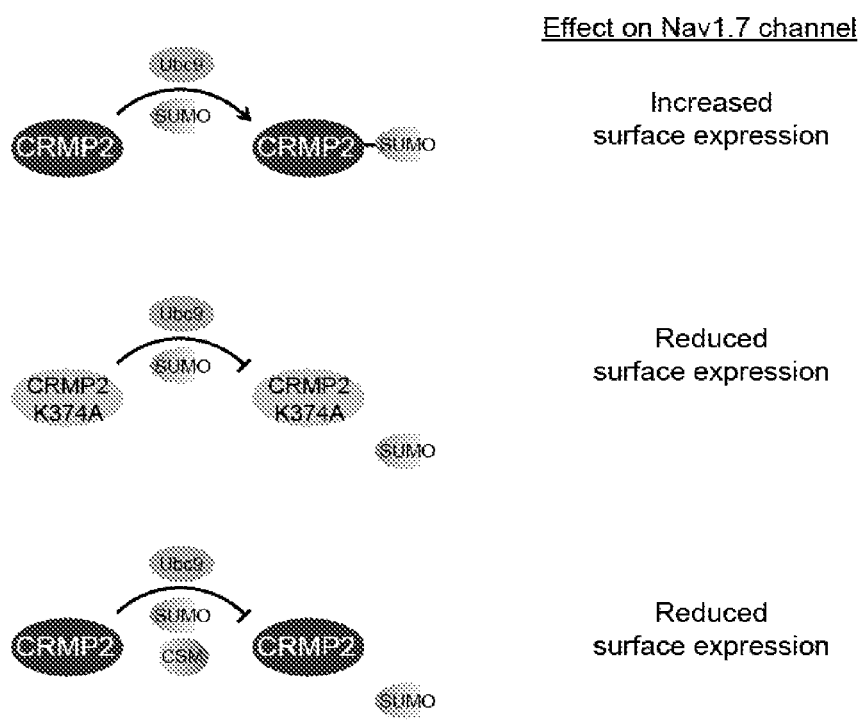
FIG. 3. Schematic illustrating regulation of Nav1.7 by CRMP2. Data disclosed herein shows that CRMP2 is SUMOylated by the E2 ubiquitin conjugating enzyme Ubc9. CRMP2 SUMOylation leads to an increase in current density via increased cell surface trafficking of Nav1.7. Elimination of the CRMP2 SUMOylation site (K374) or introduction of decoy peptides encompassing the CRMP2 SUMOylation motif (CSM) into cell results in decreased Nav1.7 current density via a decrease in surface expression of Nav1.7. By manipulating CRMP2 SUMOylation, the mechanism by which SUMOylation choreographs Nav1.7 trafficking is determined. The disclosed peptides can be used to modulate pain behavior, inflammation and a neuropathy.

Post-translational modifications, particularly phosphorylation (FIG. 2), are involved in directing CRMP2 interactions and regulating the function of the partner proteins. For instance, phosphorylation by cyclin dependent kinase 5 (Cdk5) enhances interaction between CRMP2 and voltage-gated calcium channels to modulate calcium influx. Phosphorylation by glycogen synthase kinase 3β or Rho-associated protein kinase (ROCK) lowers the capability of CRMP2 to bind to tubulin heterodimers leading to microtubule destabilization, culminating in axon retraction/growth cone collapse.

Of particular relevance here, protein phosphorylation often impacts subsequent SUMOylation in many proteins. For example, direct phosphorylation by protein kinase C and SUMOylation of kainate receptor subunit GluK2 are intimately linked in regulating the surface expression and function of GluK2-containing kainite receptors. However, it is unknown whether phosphorylation modulates SUMOylation of CRMP2 to alter Nav1.7 trafficking and activity.

The modification of CRMP2 SUMOylation represents a mechanism of controlling Nav1.7, indicating that surface expression of peripherally expressed Nav1.7 can possibly be targeted exclusively. Disclosed herein are studies indicating that decreasing Nav1.7 trafficking in primary DRG neurons, in contrast to directly blocking the channel, is an effective strategy for developing inhibitors against Nav1.7 for combating pain (see Example Section provided below). Building upon this finding, the inventors have developed a peptide therapeutics that can recapitulate the decrement of Nav1.7 current density observed upon loss of CRMP2 SUMOylation. The peptide therapeutic alleviates stimulus-dependent neuropathic hypersensitivity by preventing CRMP2-SUMOylation mediated trafficking of Nav 1.7 function, a new approach towards the management of chronic pain.

II. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Administering: To provide or give a subject an agent, such as a therapeutic agent, by any effective route. Exemplary routes of administration include, but are not limited to, injection (such as subcutaneous, intramuscular, intradermal, intraperitoneal, intrathecal, epidural, and intravenous), oral, intraductal, sublingual, rectal, transdermal, intranasal, vaginal and inhalation routes.

Analgesic agent: An analgesic agent may be either an anesthetic that provides insensitivity to pain, or an agent that diminishes sensitivity to pain without necessarily ablating pain perception entirely. In some examples, the disclosed peptides are analgesic agents. In other examples, the disclosed peptides are anesthetic.

Blood-brain barrier (BBB): The barrier formed by epithelial cells in the capillaries that supply the brain and central nervous system. This barrier selectively allows entry of substances such as water, oxygen, carbon dioxide, and nonionic solutes such as glucose, alcohol, and general anesthetics, while blocking entry of other substances. Some small molecules, such as glucose and amino acids, are taken across the barrier by specific transport mechanisms.

Brain injury: Any injury to one of more types of intracranial tissues, regardless of injury mechanism. While the most common injury mechanisms are blunt or penetrating trauma, other injuries may include surgical trauma, radiation, electricity/lightning, acoustic energy, or a blast wave injury in its primary, secondary, tertiary, or quaternary forms. Brain injury includes the injury mechanism and any post-injury sequelae, such as the physical, biochemical, inflammatory, or immunologic responses to injury, whether such sequelae occur as an immediate, delayed, or prolonged response. Some injury mechanisms, injury responses, and post-injury clinical syndromes are discussed in CG Goetz (editor), *Textbook of Clinical Neurology,* 3$^{rd}$ Edition, 2007, Chapter 51. Additional mechanisms or responses include, but are not limited to cavitation, shear, strain, or strain rate mediated injuries; blood-brain barrier response; acute or chronic inflammatory responses; and altered neurogenesis, neuronal migration, or stem cell response. Additional post-injury clinical syndromes could include changes in mood, anxiety, cognition, perception, consciousness, or reality testing.

Depressive Disorder: A mood disorder characterized by a predominantly sad or depressed mood, typically but not always of two or more weeks' duration. A depressive disorder also has other signs or symptoms accompanying a sad or depressed mood, including one or more of: decreased energy, appetite changes, weight gain or loss, insomnia or hypersomnia, recurrent thoughts or death, thoughts of suicide, loss of interest in usual activities, slowed thinking or cognitive speed, increased speech latency, decreased volume of speech, excessive or inappropriate guilt, diminished concentration, feeling sluggish, and slower than normal motor activity (such as gross motor, fine motor, speech). Depressive disorders can be accompanied by perceptual disturbances. Depressive disorders can be caused by a medical disorder (e.g., endocrine disorders, lupus), medication side-effect (e.g., interferon), substance use disorder, neurologic disorder (e.g., seizure disorder, traumatic brain injury), or have no clear cause.

Cancer: A malignant neoplasm that has undergone characteristic anaplasia with loss of differentiation, increased rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

Cell Penetrating Motif: An amino acid motif which facilitates the ability of a peptide to penetrate/cross a cell membrane.

Effective amount: An amount of a compound or a combination of compounds sufficient to achieve a desired effect, for example to treat or inhibit a disease or condition in a subject. The amount of a compound or combination of compounds which is an effective amount will vary depending on the compound and the desired effect. An effective amount can be determined by one of ordinary skill in the art.

Nociception: The neural processes of encoding and processing noxious stimuli, for example the afferent activity produced in the peripheral and central nervous system by stimuli that have the potential to damage tissue. This activity is initiated by nociceptors (also called pain receptors), that can detect mechanical, thermal or chemical changes above a set threshold. Once stimulated, a nociceptor transmits a signal along the spinal cord, to the brain. In some embodiments, nociception refers to the perception of pain.

Peptide: Any compound composed of amino acids or amino acid analogs chemically bound together. Peptide as used herein includes oligomers of amino acids, amino acid analog, or small and large peptides, including polypeptides or proteins. Any chain of amino acids, regardless of length or post-translational modification (such as glycosylation or phosphorylation). In one example, a peptide is two or more amino acids joined by a peptide bond. Typically, a peptide consists of fewer than fifty amino acids; for example, consisting of approximately 3 to approximately 20 amino acids, consisting of approximately 7 to approximately 18 amino acids, consisting of approximately 7 to approximately 20 amino acids.

"Peptide" applies to amino acid polymers to naturally occurring amino acid polymers and non-naturally occurring amino acid polymer as well as in which one or more amino acid residue is a non-natural amino acid, for example a artificial chemical mimetic of a corresponding naturally occurring amino acid.

A "polypeptide" is a polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "residue" or "amino acid residue" includes reference to an amino acid that is incorporated into a protein, polypeptide, or peptide.

The term "soluble" refers to a form of a polypeptide that is not inserted into a cell membrane.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine Pharmaceutically acceptable carrier: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the agents disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Post-Traumatic Stress Syndrome (PTSD): A disorder that can occur after experiencing a traumatic event that leaves a subject feeling scared, confused, and/or angry to the extent that daily activities are difficult to perform. A traumatic event can include combat or military exposure, child sexual or physical abuse, terrorist attacks, sexual or physical assault, serious accidents, and natural disasters (such as a fire, tornado, hurricane, flood, or earthquake). In an example, PTSD is defined by the Diagnostic and Statistical Manual (DSM), Fourth-Edition, Text Revision, published by the American Psychiatric Associating (DSM-IV-TR).

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a disclosed peptide capable of regulating Nav1.7 will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a peptide are typically characterized by possession of at least about 75%, for example at least about 80%, 90%, 95%, 96%, 97%, 98% or 99% sequence identity counted over the full length alignment with a particular amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and non-human mammals.

Substitution: The replacement of one thing with another. With reference to an amino acid in a polypeptide "substitution" means replacement of one amino acid with a different amino acid.

Traumatic Brain Injury (TBI): A disorder caused by an injury to the head which results in a post-injury disturbance in mood, anxiety, cognitive function, pain, balance, oculomotor function, level of consciousness, or memory. As used in this document, TBI is inclusive of all reported injury mechanisms (penetrating, blast, blunt), any post-injury changes, the inflammatory—immunologic response commonly observed after injury or illness, or any iatrogenic causes or consequences. Examples of iatrogenic causes or consequences include changes in the brain as a result of surgery, chemotherapy for cancer, radiation therapy, or a medication side-effect.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

III. Peptides and Nucleic Acids

Disclosed herein are CRMP2 SUMOylation motif (CSM-1) peptides which regulate collapsin response mediator protein 2 (CRMP2)-small ubiquitin-like modifier (SUMO)ylation mediated trafficking of Nav1.7 function and can be used to modulate disorders, conditions and diseases regulated by Nav1.7. Methods for preparing and using these peptides for the treatment of conditions that involve pain, such as acute and chronic pain including inflammatory and neuropathic pain states, are provided. Also disclosed are methods for delivering analgesia or relief from pain to an individual by administering to the bloodstream an effective amount of an analgesic molecule, which is a disclosed peptide. In certain aspects, methods of treating pain due to cancer are disclosed. Methods for the treatment and prevention or amelioration of neurological conditions, such as Parkinson's Disease, Alzheimer's Disease, Pick's Disease, and Chronic Fatigue Syndrome, and treatment of emotional or mood disorders. In certain embodiments, the peptides of the present disclosure comprise the amino acid sequence KMD and are typically between 3 and 18 amino acids in length, more preferably between 5 and 8 amino acids in length.

In some embodiments, the disclosed peptides are formulated into compositions, which compositions may be used for the treatment of neurological conditions, including conditions that involve pain, such as acute and chronic pain including inflammatory and neuropathic pain states. The compositions may include one or more additional active agents, such as anti-inflammatory agents or anti-pain agents, as well as one or more inactive agents, which may include carriers, delivery vehicles, binding agents, diluents, disintegrants, lubricants, buffers, and other pharmaceutically acceptable excipients.

In specific embodiments, the disclosed peptides comprise three to twenty amino acids, such as 3 to 7, 15 to 18, 4 to 8, including 3, 4, 5, 6, 7, 8, 9, 10, 11, 12, 13, 14, 15, 16, 17, 18, 19, or 20 amino acids, in which the three to twenty amino acids comprise the amino acid sequence KMD. The disclosed peptides are capable of preventing collapsin response mediator protein 2 (CRMP2)-small ubiquitin-like modifier (SUMO)ylation mediated trafficking of voltage gated sodium channel 1.7 (Nav1.7) function. In one particular example, the CSM-1 peptide comprises three to eight amino acids. In one example, the CSM-1 peptide comprises an amino acid sequence with at least 90% sequence identity, such as 90%, 91%, 92%, 93%, 94%, 95%, 96%, 97%, 98%, 99% or 100% sequence identity to the amino acid sequence GKMDENQ (CSM-1S; SEQ ID NO: 1). In some examples, the CSM-1 peptide comprises the amino acid sequence GKMDENQ (CSM-1S; SEQ ID NO: 1). In some examples, the CSM-1 peptide consists of the amino acid sequence GKMDENQ (CSM-1S; SEQ ID NO: 1). In one example, the peptide comprises an amino acid sequence with at least 90% sequence identity, such as 90%, 91%, 92%, 93%, 94%, 95%, 96%, 97%, 98%, 99% or 100% sequence identity to the amino acid sequence WDKAVVTGKMDENQFVAV (CSM-1L; SEQ ID NO: 2). In some examples, the CSM-1 peptide comprises the amino acid sequence WDKAVVTGKMDENQFVAV (CSM-1L; SEQ ID NO: 2). In some examples, the CSM-1 peptide consists of the amino acid sequence WDKAVVTGKMDENQFVAV (CSM-1L; SEQ ID NO: 2).

In some examples, a disclosed CSM-1 peptide includes one or more modifications, for example to increase lipophilicity of the peptide. In one example, the hydroxyl group of a tyrosine residue is acetylated in a CSM-1 peptide. In other examples, the CSM-1 peptide includes one or more modifications to increase stability of the peptide. In some embodiments, the non-opioid CSM-1 peptide includes one or more D-amino acids (such as 1, 2, 3, 4, 5, or 6 D-amino acids).

In some examples, a CSM-1 peptide is conjugated to a moiety by an ester bond. In some examples, the moiety is an alcohol, a sugar, a lipid, or dehydroascorbic acid. One of ordinary skill in the art can select an appropriate moiety to include in the conjugate with a CSM-1 peptide. In some examples, the moiety is one that can facilitate transport across or through the BBB, for example through a cellular transporter (for example, via a glucose transporter) or due to lipophilicity (for example, a lipid). In some examples, a CSM-1 peptide is conjugated to a cell penetrating motif such as a TAT peptide (Vives et al., *J. Biol. Chem.* 1997, 272, 16010-16017, which is hereby incorporated by reference in its entirety). In some examples, a CSM-1 peptide is conjugated to a cell penetrating motif such as a membrane translocating sequence from the FGF receptor (Delli Bovi et al. 1987 Cell. 1987 August 28; 50(5):729-37.; Rojas et al. 1996 J Biological Chemistry 1996 November 1; 271(44): 27456-61.; Rojas et al. 1998 Nature Biotechnol. 1998 April; 16(4):370-5.; each of which is hereby incorporated by reference in its entirety. In some examples, a CSM-1 peptide is conjugated to a homopolymer or peptide containing a high percentage of cationic amino acids (Mitchell et al., *J. Pept. Res.* 2000, 56, 318-325, which is hereby incorporated by reference in its entirety). In some examples, a CSM-1 peptide is conjugated to a model amphipathic peptide, MAP (Oehlke et al., *Biochim. Biophys. Acta* 1998, 1414, 127-139, which is hereby incorporated by reference in its entirety). In some examples, a CSM-1 peptide is conjugated to a cell penetrating motif with one of the following amino acid sequences:

(a) GRKKRRQRRRPPQ; (SEQ ID NO: 3)

(b) RQIKIWFQNRRMKWKK; (SEQ ID NO: 4)

(c) LLIILRRRIRKQAHAHSK; (SEQ ID NO: 5)

(d) RGGRLSYSRRRFSTSTGR; (SEQ ID NO: 6)

(e) RRRRRRRR; (SEQ ID NO: 7)

(f) GRRRRRRRRPPQ; (SEQ ID NO: 8)

(g) AAVALLPAVLLALLAP; (SEQ ID NO: 9)

(H) KLALKLALKALKAALKLA; (SEQ ID NO: 10)

(i) TRRQRTRRARRNR; (SEQ ID NO: 11)

(j) PLSSIFSRIGDP; (SEQ ID NO: 12)

(k) MALNLGWLLALFVTMWTDVGLCKKRPKP; (SEQ ID NO: 13)

(l) AGYLLGKINLKALAALAKKIL; (SEQ ID NO: 14)

or (m) PLSSIFSRIGDP. (SEQ ID NO: 15)

In addition, in some examples the moiety is one that is familiar to the central nervous system (CNS), for example, the moiety is one known to be generally non-toxic to the CNS. In some embodiments, the moiety is an alcohol, such as ethanol, diethylaminoethanol, benzyl alcohol, propanol, or butanol. In one non-limiting example, the moiety is ethanol. In other embodiments, the moiety is a sugar, such as glucose or fructose. Appropriate sugars include those that can be transported across the BBB by one of the family of glucose transporters (e.g., GLUT1 to GLUT5). In some examples, the moiety is directly conjugated to the CSM-1 peptide. In other examples, the moiety and the CSM-1 peptide are conjugated via a linker molecule.

The disclosed peptides can be synthesized by methods known to one of ordinary skill in the art including those described in the Examples. CSM-1 peptides can be produced by standard techniques, such as solid phase synthesis (for example, utilizing an automated peptide synthesizer or manual peptide synthesis), standard solution synthesis or simultaneous multiple peptide synthesis. See, e.g., Merrifield, *J. Am. Chem. Soc.* 85:2149-2154, 1964; Bodanszky, *Principles of Peptide Synthesis*, 2nd Edition, Springer, 1993; Pennington and Dunn, *Peptide Synthesis Protocols*, Humana Press, 2005.

Nucleic acid molecules encoding the peptides disclosed herein are also provided. These nucleotides include DNA, cDNA and RNA sequences which encode the peptide of interest.

A nucleic acid molecule encoding a disclosed peptide can be cloned or amplified by in vitro methods, such as the polymerase chain reaction (PCR), the ligase chain reaction (LCR), the transcription-based amplification system (TAS), the self-sustained sequence replication system (3SR) or the Qβ replicase amplification system (QB). A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, N Y, 1989).

CSM-1-encoding nucleic acid molecules also can be isolated by screening genomic or cDNA libraries with probes selected from the sequences of the desired nucleotide under stringent hybridization conditions.

The nucleic acid molecules encoding a disclosed CSM-1 peptide include nucleic acid molecules encoding a CSM-1 peptide that are incorporated into a vector, such as an autonomously replicating plasmid or virus, or that exist as a separate molecule (e.g., a cDNA) independent of other sequences. The nucleotides of the disclosure can be ribonucleotides, deoxyribonucleotides, or modified forms of either nucleotide. The term includes single and double stranded forms of DNA.

DNA sequences encoding a CSM-1 peptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

A nucleic acid sequence encoding CSM-1 peptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The nucleic acid sequences encoding a CSM-1 peptide can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA can be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed nucleotide sequences encoding a CSM-1 peptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Further provided are compositions comprising one or more of the CSM-1 peptides disclosed herein. The provided compositions further include compositions comprising a CSM-1 fusion protein disclosed herein. Also provided are compositions comprising a nucleic acid molecule encoding a CSM-1 peptide. In some embodiments, the nucleic acid molecule is a vector encoding a CSM-1 peptide. In some examples, a disclosed CSM-1S DNA and any variant of this sequence is delivered in a lentiviral or adeno-associated virus similar to that described Fischer et al. (Gene therapy 21, 44-51, 2014) which is hereby incorporated by reference in its entirety.

Formulations

The compositions of the present disclosure may further comprise a pharmaceutically acceptable carrier/excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, 21$^{st}$ Edition, E. W. Martin (Mack Publishing Co., Easton, Pa., 2005) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this disclosure. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars; starches; cellulose and its derivatives; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutically acceptable excipients which may be used in the manufacture of pharmaceutical compositions also include, but are not limited to, inert diluents, dispersing and/or granulating agents, surface active agents and/or emulsifiers, disintegrating agents, binding agents, preservatives (e.g., antioxidants, chelating agents, antimicrobial preservatives, antifungal preservatives, alcohol preservatives, acidic preservatives, and the like), buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

In certain embodiments, the composition further comprises one or more sugars. The term "sugar" as used herein refers to a natural or an unnatural monosaccharide, disaccharide, oligosaccharide, or polysaccharide, comprising one or more triose, tetrose, pentose, hexose, heptose, octose, or nonose saccharides. Sugars may include substances derived from saccharides by reduction of the carbonyl group (alditols), by oxidation of one or more terminal groups to carboxylic acids (aldonic acids), or by replacement of one or more hydroxyl group(s) by a hydrogen (deoxy sugars), an amino group (amino sugars), a thiol group (thio sugars), an acylamino group, a sulfate group, a phosphate group, or similar heteroatomic group; or any combination of the foregoing modifications. The term sugar also includes derivatives of these compounds (i.e., sugars that have been chemically modified by acylation, alkylation, and formation of glycosidic bonds by reaction of sugar alcohols with aldehydes or ketones, etc.). Sugars may be present in cyclic (oxiroses, oxetosesm furanoses, pyranoses, septanoses, octanoses, etc.) form as hemiacetals, hemiketals, or lactones;

or in acyclic form. The saccharides may be ketoses, aldoses, polyols and/or a mixture of ketoses, aldoses and polyols.

Exemplary sugars include, but are not limited to glycerol, polyvinylalcohol, propylene glycol, sorbitol, ribose, arabinose, xylose, lyxose, allose, altrose, mannose, mannitol, gulose, dextrose, idose, galactose, talose, glucose, fructose, dextrates, lactose, sucrose, starches (i.e., amylase and amylopectin), sodium starch glycolate, cellulose and cellulose derivatives (i.e., methylcellulose, hydroxypropyl cellulose, hydroxyethyl cellulose, hydroxyethylmethyl cellulose, carboxymethyl cellulose, cellulose acetate, cellulose acetate phthalate, croscarmellose, hypomellose, and hydroxypropyl methyl cellulose), carrageenan, cyclodextrins (e.g., hydroxypropyl-gamma-CD), dextrin, polydextrose, and trehalose. In certain embodiments, the sugar is selected from lactose anhydrous, lactose monohydrate, trehalose and hydroxypropyl-gamma-CD.

In certain embodiments, the composition further comprises one or more polymers. In certain preferred embodiments, the polymer is polyvinyl alcohol (PVA). Other Examples include gelatin, polyvinyl pyrolidone (PVP), albumin, and polyethyleneimine (PEI), acacia gum, cellulose derivatives, calcium polypectate, maleic anhydride derivatives, polyacrylic and methacrylic acid, phospholipids, polyglycolide and lactide derivatives, starch, alginates and alginic acid, calcium caseinate, carrageenan, pectins, polyhexametaphosphate, polyvinyl acetate, polyvinyl alcohol, and the like; mixtures thereof; and the like.

In certain embodiments, the composition further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite ($NaHSO_3$).

In certain embodiments, the one or more preservative comprises a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises an alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient (i.e., a glycosylated deltorphin variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

In some examples, a preferred dosage forms include oral and parenteral dosage forms. Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the disclosed compositions are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. Nos. 5,912,014, 6,086,918 and 6,673,574 (the disclosure of each of these patents is hereby incorporated herein by reference).

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present disclosure contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the disclosure may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the disclosure formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the disclosure may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in Remington: The Science and Practice of Pharmacy 21.sup.st ed., Lippincott Williams & Wilkins, 2005.

In some embodiments, the disclosed peptides are included in a controlled release formulation, for example, a microencapsulated formulation. Various types of biodegradable and biocompatible polymers can be used, and methods of encapsulating a variety of synthetic compounds, proteins and nucleic acids, have been well described in the art (see, for example, U.S. Pat. Publication Nos. 2007/0148074; 2007/0092575; and 2006/0246139; U.S. Pat. Nos. 4,522, 811; 5,753,234; and 7,081,489; PCT Publication No. WO/2006/052285; Benita, *Microencapsulation: Methods and Industrial Applications,* $2^{nd}$ ed., CRC Press, 2006).

In other embodiments, a disclosed peptide is included in a nanodispersion system. Nanodispersion systems and methods for producing such nanodispersions are well known to one of ordinary skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In some examples, the nanodispersion is prepared using the solvent evaporation method. See, e.g., Kanaze et al., *Drug Dev. Indus. Pharm.* 36:292-301, 2010; Kanaze et al., *J. Appl. Polymer Sci.* 102:460-471, 2006.

In other examples, the disclosed compounds and pharmaceutical compositions are formulated as a depot preparation for administration by implantation or intramuscular injection. The active ingredient may be formulated with suitable polymeric or hydrophobic materials (for example, as an emulsion in an acceptable oil) or ion exchange resins, or as sparingly soluble derivatives, (such as a sparingly soluble salt). Alternatively, transdermal delivery systems manufactured as an adhesive disc or patch which slowly releases the active compounds for percutaneous absorption are used. Permeation enhancers may be used to facilitate transdermal penetration of the composition. Transdermal patches are described for example, in U.S. Pat. Nos. 5,407,713; 5,352, 456; 5,332,213; 5,336,168; 5,290,561; 5,254,346; 5,164, 189; 5,163,899; 5,088,977; 5,087,240; 5,008,110; and 4,921, 475.

In some examples, a disclosed peptide includes a pharmaceutically acceptable salt of such compounds. "Pharmaceutically acceptable salts" of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts are also inclusive of the free acid, base, and zwitterionic forms. Description of suitable pharmaceutically acceptable salts can be found in *Handbook of Pharmaceutical Salts, Properties, Selection and Use*, Wiley VCH (2002).

The dosage form of the pharmaceutical compositions will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The compounds of this disclosure can be administered to humans or other animals on whose tissues they are effective in various manners such as orally, intravenously, intramuscularly, intraperitoneally, intranasally, intradermally, transdermally, intrathecally, epidurally, sublingually, subcutaneously, via inhalation or via suppository. In one non-limiting example, the compound is administered orally. In another non-limiting example, the compound is administered intravenously, transdermally, intrathecally, epidurally, or sublingually. The particular mode of administration and the dosage regimen is selected by the attending clinician, taking into account the particulars of the case (e.g. the subject, the disease or condition involved, and whether the treatment is prophylactic). Treatment can involve daily or multi-daily doses of compound(s) over a period of a few days to months, or even years. One of ordinary skill in the art can identify appropriate doses for the CSM-1 peptides of use in the disclosed methods. The amount administered will be dependent on factors such as the subject being treated, the type and severity of the condition, and the mode of administration.

A pharmaceutical composition that includes one or more disclosed peptides can be formulated in unit dosage form, suitable for individual administration of precise dosages. In one specific, non-limiting example, a unit dosage contains from about 10 µg to about 5 g or more of one or more CSM-1 peptides (such as about 50 µg to about 1 mg, about 100 µg to about 10 mg, about 1 mg to about 2.5 g, about 10 mg to about 1 g, or about 100 mg to about 500 mg). In some examples, a unit dosage contains about 10 µg or more of one or more CSM-1 peptides (such as about 10 µg, 25 µg, 50 µg, 75 µg, 100 µg, 200 µg, 250 µg, 500 µg, 750 µg, 1 mg, 2.5 mg, 5 mg, 7.5 mg, 10 mg, 25 mg, 50 mg, 100 mg, 250 mg, 500 mg, 750 mg, 1 g, 1.5 g, 2 g, 2.5 g, 3 g, 4 g, 5 g, or more). The amount of active compound administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

In some embodiments, an effective amount of one or more disclosed CSM-1 peptides is administered to a subject, thereby altering nociception in the subject. In some examples, administration of a CSM-1 peptide to a subject decreases nociception or pain perception (for example, the CSM-1 peptide is an analgesic agent). In some examples, an effective amount of a CSM-1 peptide is about 1 µg/kg to about 100 mg/kg (for example, about 1 µg/kg to about 10 mg/kg, about 10 µg/kg to about 5 mg/kg, about 100 µg/kg to about 1 mg/kg, about 1 mg/kg to about 50 mg/kg, about 10 mg/kg to about 25 mg/kg, or about 20 mg/kg to about 100 mg/kg). In some examples, an effective amount is about 1 µg/kg or more of a peptide (such as about 1 µg/kg, 5 µg/kg, 10 µg/kg, 25 µg/kg, 50 µg/kg, 75 µg/kg, 100 µg/kg, 250 µg/kg, 500 µg/kg, 750 µg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 50 mg/kg, or more). In a specific example, an effective amount of a CSM-1 peptide is about 5 mg/kg to about 20 mg/kg, such as about 10 mg/kg. In another specific example, an effective amount of a CSM-1 peptide is about 1 µg/kg to about 1 mg/kg, such as about 10 µg/kg to 100 µg/kg or about 200 µg/kg to 600 µg/kg. One of ordinary skill in the art can extrapolate from an animal dose (such as a rat or mouse) to an appropriate human dose, such as for use in clinical trials for determining pharmacokinetics and dosing (see, e.g., Reagan-Shaw et al., *FASEB J.* 22:659-661, 2008).

An effective amount of a CSM-1 peptide can be the amount of the CSM-1 peptide necessary to alter nociception (such as to treat or inhibit pain, for example to decrease pain or pain perception) in a subject. An effective amount of a CSM-1 peptide can be administered in a single dose, or in several doses, for example weekly, bi-weekly, daily, or 2, 3, 4, or 5 more times daily, during a course of treatment. One of ordinary skill in the art can determine the effective amount of a CSM-peptide based for example, on the subject being treated, the severity and type of the affliction, the manner of administration, and the physicochemical properties of the CSM-peptide.

In particular examples, prior to, during, or following administration of an effective amount of a CSM-1 peptide, the subject can receive one or more other therapies. In one example, the subject receives one or more additional treatments to alter nociception, such as one or more pain-relieving therapeutics other than a CSM-1 peptide (for example, a non-steroidal anti-inflammatory therapeutic). The combined administration of the CSM-1 peptide and additional pharmaceutical agents includes administering the additional agent either sequentially with the CSM-1 peptide, e.g., the treatment with one agent first and then the second agent, or administering both agents at substantially the same time, e.g., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, e.g., physically mixed, or in separate doses administered at the same time.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the disclosure are kits that comprise one or more disclosed complexes and/or compositions. Kits are typically provided in a suitable container (e.g., for example, a glass, foil, plastic, or cardboard package). In certain embodiments, a kit may include one or more pharmaceutical excipients, pharmaceutical additives, therapeutically active agents, and the like, as described herein. In certain embodiments, a kit includes means for proper administration, such as, for example, graduated cups, syringes, needles, cleaning aids, and the like. In certain embodiments, a kit includes instructions for proper administration and/or preparation for proper administration.

IV. Methods of Use

The peptides, compositions and formulations of the present disclosure are useful for the prevention and/or treatment of disorders, conditions and diseases regulated by Nav1.7, including, but not limited to, acute and chronic pain, nociceptic pain, cancer pain, neuralgia, myalgia, burn pain, arthritic pain, bowel inflammation pain, bone and osteoporosis pain, and inflammatory pain, such as neuroinflammation that accompanies some kinds of nerve injury (e.g., diabetic neuropathy). Other conditions treatable as part of the present peptides include neurological disorders such as Parkinson's Disease, Alzheimer's Disease, Pick's Disease, and Chronic Fatigue Syndrome. The disclosed peptides can also be used to treat emotional and mood disorders, such as depression, PTSD, anxiety, addiction and obsessive compulsive disorder. The disclosed peptides can also be used to treat pain associated with a traumatic brain injury. In some examples, the disclosed peptides are used to treat pain associated with a migraine headache. In some examples, the disclosed compositions are administered to a subject with or likely to develop a substance use disorder (SUD) or other condition/disease that opioid therapy cannot be administered.

In general terms, treating pain can include inhibiting, suppressing, down-regulating, blocking, preventing or otherwise modulating the activity of the Nav1.7. In some embodiments, methods of reducing one or more signs or symptoms associated with chronic pain are disclosed. In some examples, the disclosed peptides and compositions are utilized to treat chronic pain associated with a particular condition, disease or disorder that is typically treated by chronic opioid therapy. In some examples, the disclosed compositions are utilized to treat chronic pain in addition to a traditional pain therapy, such as chronic opioid therapy in that the combination allows the traditional pain therapy to be diminished.

In one example, a method includes administering to the subject an effective amount, such as a therapeutically effective amount, of one or more of the disclosed peptides and/or compositions, thereby reducing or inhibiting one or more symptoms associated with the disorder, condition and/or disease regulated by Nav1.7.

Also disclosed is a method for modulating Nav1.7 activity including contacting a cell, (e.g., a cell present in a mammal, such as a human) with a therapeutically effective amount of one or more of the disclosed peptides or compositions in which the composition modulates the activity of Nav1.7 in the treated cell relative to Nav1.7 activity in an untreated cell, thereby reducing or inhibiting one or more signs or symptoms associated with the Nav1.7 disorder, condition and/or disease. In one example, modulating activity of Nav1.7 includes preventing, inhibiting and/or reducing collapsin response mediator protein 2 (CRMP2)-small ubiquitin-like modifier (SUMO)ylation mediated trafficking of voltage gated sodium channel 1.7 (Nav1.7) function as compared to that occurring in an untreated cell. In an example, contacting the cell with one or more agents comprises administering the one or more agents to the mammal, such as a human.

In a particular example, the compound or a pharmaceutical composition comprising the conjugate readily penetrates the blood-brain barrier when peripherally administered. Compounds of this disclosure which cannot penetrate the blood-brain barrier can be effectively administered by an intraventricular route. In a further example, the pharmaceutical composition comprises a compound of the disclosure and a pharmaceutically acceptable carrier that facilitates it to cross the blood-brain barrier.

In some examples, the methods of use can include selecting a subject in need of treatment. For example, studies can be performed to identify a subject at risk of or as being afflicted with disorders, conditions and diseases regulated by Nav1.7, including, but not limited to, acute and chronic pain, nociceptic pain, cancer pain, neuralgia, traumatic brain injury pain, myalgia, burn pain, arthritic pain, bowel inflammation pain, bone and osteoporosis pain, and inflammatory pain, such as neuroinflammation that accompanies some kinds of nerve injury (e.g., diabetic neuropathy), a neurological disorder (such as Parkinson's Disease, Alzheimer's Disease, Pick's Disease, and Chronic Fatigue Syndrome), an emotional and/or mood disorder (depression, PTSD, anxiety, addiction and obsessive compulsive disorder), and/or a substance abuse disorder. Methods of detecting a disorder, condition and/or disease regulated by Nav1.7 are known to those of skill in the art and can include methods as described herein.

Therapeutically Effective Amount

In the methods disclosed herein, an effective amount, such as a therapeutically effective amount, of a pharmaceutical composition including a composition described herein is administered to a subject with a disorder, condition and/or disease regulated by Nav1.7. Assays to determine a therapeutically effective amount of a disclosed pharmaceutical composition for inhibiting or reducing one or more signs or symptoms associated with the disorder, condition and/or disease regulated by Nav1.7 are described herein (see for example, the Examples).

In some examples, a therapeutic effective amount of a disclosed pharmaceutical composition is one in which one or more signs or symptoms associated with the disorder, condition and/or disease regulated by Nav1.7 is reduced or inhibited, such as by at least 10%, for example, about 15% to about 98%, about 30% to about 95%, about 40% to about 80%, about 50% to about 70%, including about 20%, about 30%, about 40%, about 50%, about 60%, about 70%, about 80%, about 90%, about 95%, about 98% or about 100%, less than activity in the absence of the composition.

Dosages, routes of administration of the disclosed pharmaceutical compositions for the methods of treatment are known to those of skill in the art and include, but are not limited to those described herein, including those described above and the Examples.

Exemplary Disorders, Conditions and Diseases Regulated by Nav1.7

Exemplary disorders, conditions, and diseases regulated by Nav1.7 include, but are not limited to, acute and chronic pain, nociceptive pain, cancer pain, neuralgia, myalgia, burn pain, arthritic pain, bowel inflammation pain, bone and osteoporosis pain, and inflammatory pain, such as neuroinflammation that accompanies some kinds of nerve injury (e.g., diabetic neuropathy), neurological disorders (e.g., Parkinson's Disease, Alzheimer's Disease, Pick's Disease, and Chronic Fatigue Syndrome), emotional and mood disorders (e.g., depression, PTSD, anxiety, addiction and obsessive compulsive disorder), pain associated with a traumatic brain injury, pain associated with a migraine headache, and/or a substance abuse disorder.

The following examples are provided to illustrate certain particular features and/or embodiments. These examples should not be construed to limit the disclosure to the particular features or embodiments described.

EXAMPLES

Example 1

Materials and Methods

This example provides the materials and methods utilized for the studies described herein.

Intrathecal Catheterization or Intranasal: Procedures involving these routes of administration will be performed exactly as described by us previously (Anitua, E., et al. *PloS one* 8, e73118 (2013); and Largent-Milnes, T. M., et al. *British Journal of Pharmacology* 161, 986-1001 (2010), each of which is incorporated herein by reference).

Behavioral Testing:

Tactile Hypersensitivity: Rats are acclimated in suspended, wire mesh cages for 30 minutes prior to baseline von Frey testing (pre- and post-nerve ligation or sham-operation). Following administration of compound or vehicle (t=0) responses will be assessed to calibrated von Frey filaments (0.4-15.0 g) probed perpendicularly on the plantar surface of the left hind paw (ipsilateral to the SNL) for 7 seconds, at 15 min intervals for the first 60 min utilizing the up-down method used previously (Chaplan et al., *J. Neurosci. Methods*. 53, 55-63 (1994), which is hereby incorporated by reference). Lifting the paw, licking the paw, or vocalizing will count as positive responses to the calibrated filament. Paw withdrawal thresholds will be calculated in grams using the Dixon non-parametric as previously reported (Largent-Milnes, T. M., et al. *British Journal of Pharmacology* 161, 986-1001 (2010), which is incorporated herein by reference). Contralateral paw was not tested, as injured animals placed more body weight on the uninjured paw than on the injured side.

Thermal Hypersensitivity: Rats will be allowed to acclimate in Plexiglas holders for baseline testing (pre- and post-nerve ligation/exposure) for 30 minutes (Ugo Basile, Comerio Italy). A mobile radiant heat source will be used to direct heat to the plantar surface of the left hind paw. Paw withdrawal latencies (PWLs) will be measured in seconds with an automatic shutoff of the heat source at 33.0 s. Baselines and pre-nerve injury PWLs will be established between 20.0-25.0 s for antinociception experiments. Post-injury baselines will be obtained after the 7-day recovery period. On test days, animals will be dosed, then tested using von Frey filaments every 15 min for 60 min. The contralateral paw will not be evaluated for hypersensitivity as injured animals placed more body weight on the uninjured paw when compared to the injured side.

Spared Nerve Injury (SNI) Model: Under 2.5% isofluorane (Fisher Scientific, cat # NC9171659) in 02 anesthesia delivered at 2 L/min anesthesia, the skin on the lateral surface of the thigh is incised and a section made directly through the biceps femoris muscle exposing the sciatic nerve and its three terminal branches: the sural, common peroneal and tibial nerves (Decosterd, I. & Woolf, C. J., *Pain*. 87, 149-158 (2000) which is hereby incorporated by reference). SNI procedure comprises an axotomy and ligation of the tibial and common peroneal nerves leaving the sural nerve intact. The common peroneal and the tibial nerves are tightly-ligated with 5.0 silk and sectioned distal to the ligation, removing 2±4 mm of the distal nerve stump. Sham controls involve exposure of the sciatic nerve and its branches without any lesion. All animals were allowed 3-4 days to recover prior to any behavioral testing. Any animals exhibiting signs of motor deficiency, infection, or >10% loss in total body weight will be euthanized. This model of nerve injury results in >95% behavioral phenotype demonstrating signs of chronic pain. Any animal not demonstrating behavioral pain will be removed from the study prior to drug/vehicle testing.

Motor Skill/Sedation Assessment Using the Rotarod: Non-injured male SD rats are used to determine if the nerve injury/chronic inflammation do not confound whether the compound itself is sedative. Hence, naïve rats are trained to walk on an automated, rotating rod (8 revolutions/min; Rotamex 4/8, Columbus Instrument) for maximal cut off time of 180.0 s. Training includes placement on a non-moving rod with the instrument off for 180.0 s, placement on the non-moving rod with the machine then turned on for 180.0 s, and two additional training sessions of 180.0 s each with the rod rotating. After 10 min, baseline values are recorded for each animal. If the animal reaches the maximal time, a cut off value of 180.0 s is assigned as the observed value. Compounds are administered as described above and assessment occurs every 30 min for the first 60 to 180 mins or until return to baseline if changes are observed.

Conditioned Place Preference (CPP): The ability of a drug to be reinforcing can be measured using conditioned place preferences. The amount of time a rat spends in a putative side of conditioning is recorded before and after drug conditioning occurs. The animal is exposed to both drug and vehicle, each treatment paired with separate visual and tactile cues in two chambers of a three-chamber box, over the course of two weeks. Rat CPP boxes from San Diego Instruments (San Diego, Calif.) have end chambers customized as follows: left chamber cues: horizontal black and white stripes, smooth floor; right chamber cues: black walls, rough floor (same amount of lumens in both sides), center transition chamber: bright light, grated floor (animals spend minimal time here due to the light and graded floor). Sixteen y-axis sensors and four x-axis sensors allow for record fine motor, ambulatory, and exploratory movements. Each automated recording session is programmed to start all boxes in unison for a total of 20 min, recording in 5 min bins. Animals will be allowed to habituate for 60 min prior to baseline recordings. Two baseline recordings will be obtained on days 1 and 4 and the average used as the overall baseline, preconditioning time per chamber. Any animal showing significant preference to a chamber side prior to conditioning will be excluded. At random, animals will be separated into treatment groups and conditioned to associate one of the isolated end chambers with treatment and the opposite end chamber with vehicle. The time course of conditioning will be as follows: days 2, 3, 9, and 10 will be off days, days 5, 7, 11, and 13 will be vehicle conditioning days, and days 6, 8, 12, and 14 will be drug conditioning days. Balanced treatments to the two different chambers will be done for all drugs and vehicle treatments with all experiments being performed with experimental tester blinded to the drug administered.

DRG and Spinal Cord Removal: Following deep anesthesia with 2.5% isofluorane in 02 anesthesia delivered at 2 L/min anesthesia, animals will be decapitated and the spinal column will be severed at the pelvic girdle. The spinal cord will be expelled by hydraulic extrusion with ice-cold saline and immediately placed on ice in a glass Petri dish, and the dorsal half of the lumbar cord dissected and snap-freeze in liquid nitrogen. Tissue will be stored at −80° C. for further analysis. A small incision is made from the pelvic girdle up the back above the vertebral column with the skin and muscle displayed to the sides. The L4, L5 and L6 nerve roots are identified, vertebral wings removed and DRG identified. Cuts—both proximal and distal to the DRG—are made and ganglia are retrieved with forceps, rapidly frozen using liquid nitrogen, and then stored at −80° C. for further analysis. Tissue will be collected from all groups for comparison.

Statistics: All treatment groups will be comprised of a minimum n-value of 8-9. All data will be analyzed by non-parametric two-way analysis of variance (ANOVA; post-hoc: Neuman-Kuels) in FlashCalc (Dr. Michael H. Ossipov, University of Arizona, Tucson). When appropriate, one-way ANOVA and Students T-test will be used. Differences will be considered to be significant if p≤0.05. All data will be plotted in GraphPad Prism4 and will represent mean value±SEM unless other means are needed.

Example 2

CRMP2-Derived Anti-Nociceptive, Non-Narcotic Peptides Treat Chronic Pain

This example demonstrates the ability of CRMP2-derived anti-nociceptive, non-narcotic peptides to treat chronic pain. In particular, the inventors discovered that that (1) CRMP2 SUMOylation is important for Nav1.7 current density and surface trafficking, (2) CRMP2 SUMOylation motif (CSM) peptides prevent trafficking of Nav1.7 to the membrane surface and current density, and (3) manipulations affecting CRMP2 SUMOylation that result in Nav1.7 current decrement are anti-nociceptive in models of inflammatory and neuropathic pain without the unwanted side effects seen with opioids. Given the current dearth of tenable treatments for limiting chronic pain, the discoveries reported herein are not only innovative and of high significance, but also urgently needed.

Removal of a SUMO conjugation site (K374) in CRMP2 resulted in the loss of SUMOylated CRMP2 without compromising neurite branching, a canonical hallmark of CRMP2 function. Additionally, huwentoxin-IV-sensitive Nav1.7 currents, which predominate in a neuronal model cell line (CAD cells), were significantly reduced in cells expressing CRMP2-K374A. Increasing deSUMOylation with sentrin/SUMO-specific proteases SENP1 or SENP2 in wild type CRMP2-expressing CAD cells decreased Nav1.7 currents. Consistent with a reduction in current density, biotinylation revealed a significant reduction in surface Nav1.7 levels in CAD cells expressing CRMP2-K374A; surface Nav1.7 expression was also decreased by SENP1+ SENP2 over-expression. Currents in HEK293 cells stably expressing Nav1.7 were reduced by CRMP2-K374A in a manner dependent on the E2-conjugating enzyme Ubc9. No decrement in current density was observed in HEK293 cells co-expressing CRMP2-K374A and Nav1.1 or Nav1.3. Diminution of sodium currents, largely Nav1.7, was recapitulated in sensory neurons expressing CRMP2-K374A. This study elucidated a novel regulatory mechanism that utilizes CRMP2 SUMOylation to choreograph Nav1.7 trafficking. Also a "decoy" peptide was identified which was capable of modulating CRMP2 SUMOylation; and data disclosed herein proves the efficacy of the decoy peptide in mitigating nociception in an animal model of neuropathic pain.

CRMP2 SUMOylation motif (CSM) peptide recapitulates Nav1.7 current density decrease observed with CRMP2 SUMO null mutant. The sequence GKMDENQ (SEQ ID NO: 1; FIG. 1.B; SUMOylated lysine at position 374 underlined) in CRMP2 conforms to a canonical SUMOylation motif. The inventors determined that a peptide encompassing this region (designated CSM-1S) could serve as a "decoy" and act as a sink for the SUMOylation by Ubc9, by fusing CSM-1S to the cell penetrating transduction domain of the HIV-1 trans-activator of transcription (TAT) creating the cell permeable peptide tat-CSM-1S. If preventing CRMP2 SUMOylation were achieved by cellular dialysis of tat-CSM-1S, then we would expect Nav1.7 current density to be diminished consistent with the inventors' data. Application of 20 μM tat-CSM-1S resulted in a 53% reduction in Nav1.7 currents without any effects on fast inactivation or steady-state inactivation (FIGS. 4A-4D).

Loss of Cdk5-Mediated CRMP2 Phosphorylation Reduces Nav1.7 Currents in an Ubc9-Dependent Manner.

Figure 5:
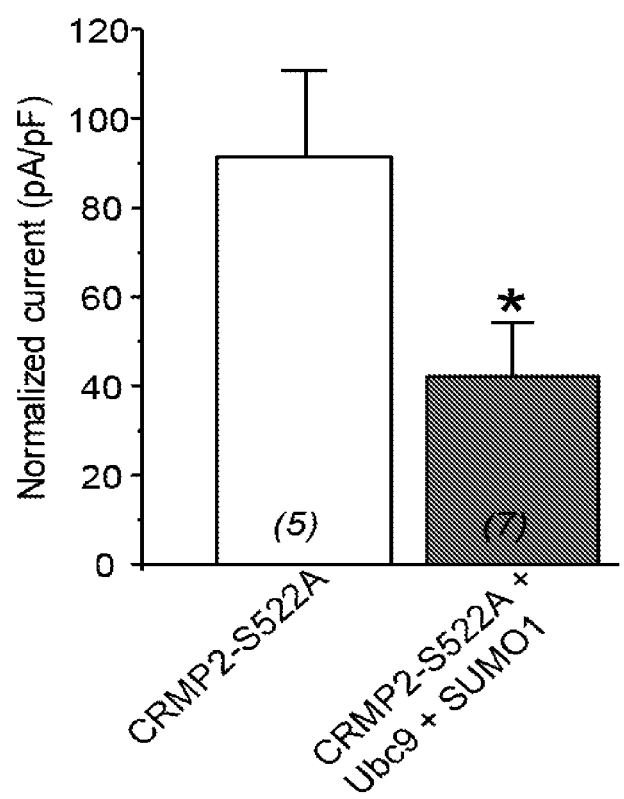
FIG. 5 Loss of Cdk5-mediated CRMP2 phosphorylation reduces Nav1.7 currents in an Ubc9-dependent manner. Summary of normalized peak currents from Nav1.7-HEK293 cells in the presence or absence of the indicated DNA constructs. Peak currents were normalized to the cell capacitance. Asterisk indicates a statistically significant difference between Cdk5 site mutant (CRMP2-S522A) and the other condition ($p<0.05$, Student's t-test).

Protein phosphorylation often impacts subsequent SUMOylation in many proteins. For example, direct phosphorylation by protein kinase C and SUMOylation of kainate receptor subunit GluK2 are intimately linked in regulating the surface expression and function of GluK2-containing kainate receptors. CRMP2 is phosphorylated at multiple sites (FIG. 2) with phosphorylation affecting functional interactions with partner proteins. The inventors recently demonstrated CRMP2 SUMOylation impacts channel trafficking. However, it is unknown whether phosphorylation modulates SUMOylation of CRMP2 to affect Nav1.7 trafficking and activity. To evaluate this, the inventors destroyed the cyclin-dependent kinase 5 (Cdk5) site S522 with an alanine, expressed this construct alone or in the presence of the CRMP2 SUMO-null construct in the additional presence of SUMOylation machinery (SUMO1 and Ubc9) in Nav1.7 HEK293 cells and assessed sodium current density. Expression of the S522A CRMP2 mutant resulted in a ~56% reduction in Nav1.7 currents only when SUMO1 and Ubc9 were co-expressed (FIG. 5). This data indicates an interplay between CRMP2 SUMOylation and phosphorylation that could impact Nav1.7 trafficking.

Using the $Na^+$ sensitive dye SBFI demonstrating its utility. The data disclosed herein show tat-CSM-1S peptide inhibits Nav1.7 currents (FIGS. 4A-4D) is entirely consistent with the inventors results demonstrating diminution of Nav1.7 currents in cells lines and in sensory neurons expressing the SUMO null CRMP2-K374A mutant. Notwithstanding that conventional patch clamp remains the sole technique with sufficiently high time resolution and sensitivity required for precise and direct characterization of ion channel properties, it is universally accepted that patch clamp is a slow, labor-intensive, and thus expensive, technique. The inventors used ouabain (1 mM), an inhibitor of $Na^+/K^+$-ATPase, to increase cytosolic $Na^+$ ($[Na^+]c$), which was then monitored using SBFI, a $Na^+$-sensitive fluorescent dye. Ouabain resulted in an increase in $[Na^+]c$ (FIG. 6A). Pre-treatment of sensory neurons with tat-CMS-1S (10 μM) strongly attenuated ouabain-induced increase in $[Na^+]c$ (FIG. 6B). The ouabain-induced increase in $[Na^+]c$ was also inhibited by tetrodotoxin (TTX, 1 μM; FIG. 6C) and Protox-II (10 μM; FIG. 6D), a specific blocker of Nav1.7, suggesting that this increase in $[Na^+]c$ is mediated by voltage-gated Na channels and, specifically, by Nav1.7. Consequently, inhibition of ouabain-induced increase in $[Na^+]c$ by tat-CMS 1S indicates that this peptide inhibits Nav1.7 effectively (FIG. 6E).

Figure 7A:
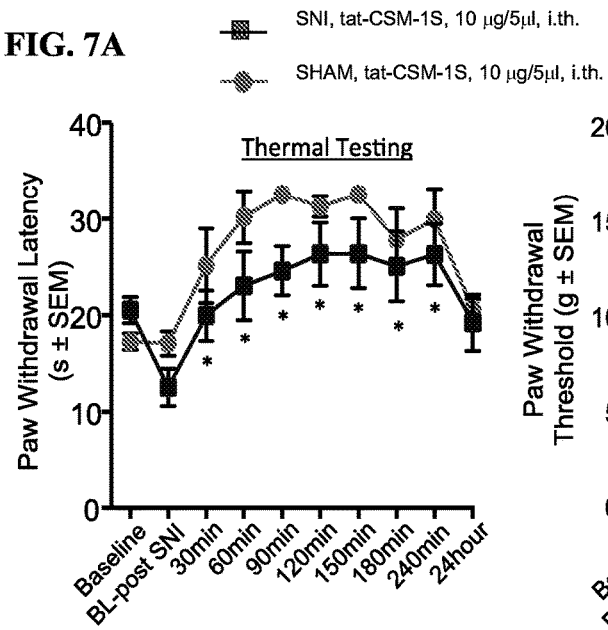
FIGS. 7A-7B. Chronic pain testing using the rat spared nerve injury (SNI) model or control (Sham) animals.
Figure 7B:
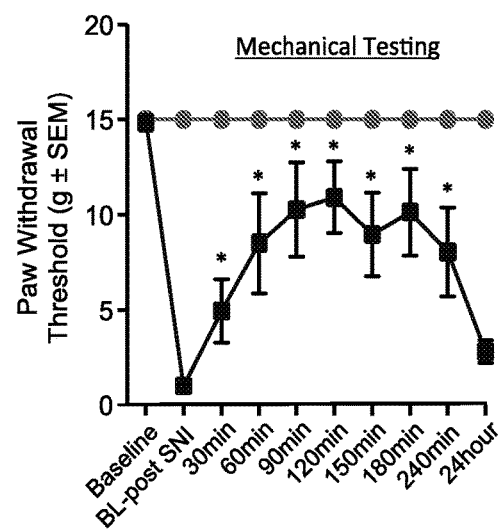
Figure 8A:
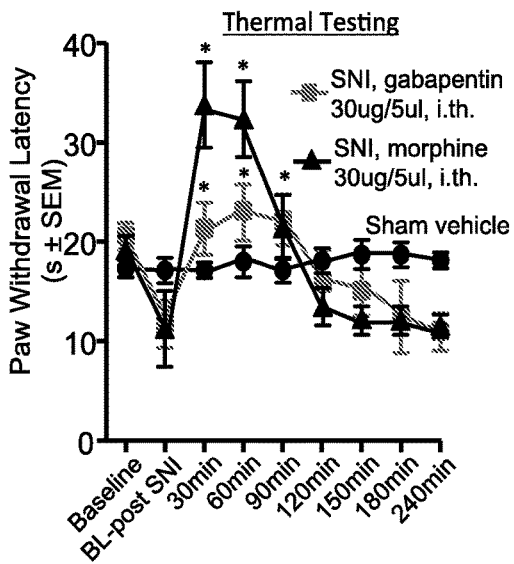
FIGS. 8A-8B. Chronic pain testing using the spared nerve injury (SNI) model or control (Sham) rats.
Figure 8B:
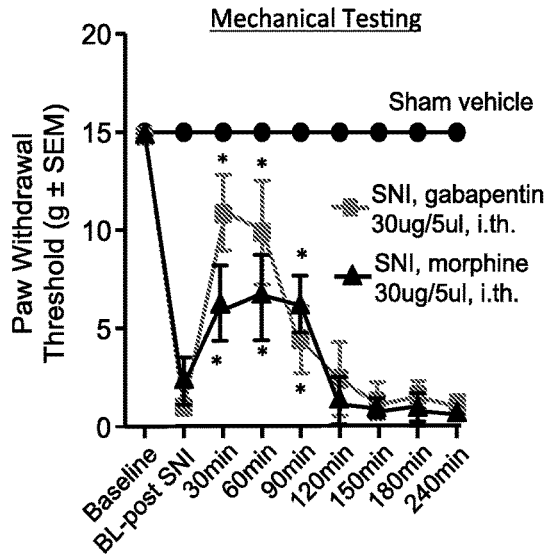
Figure 9:
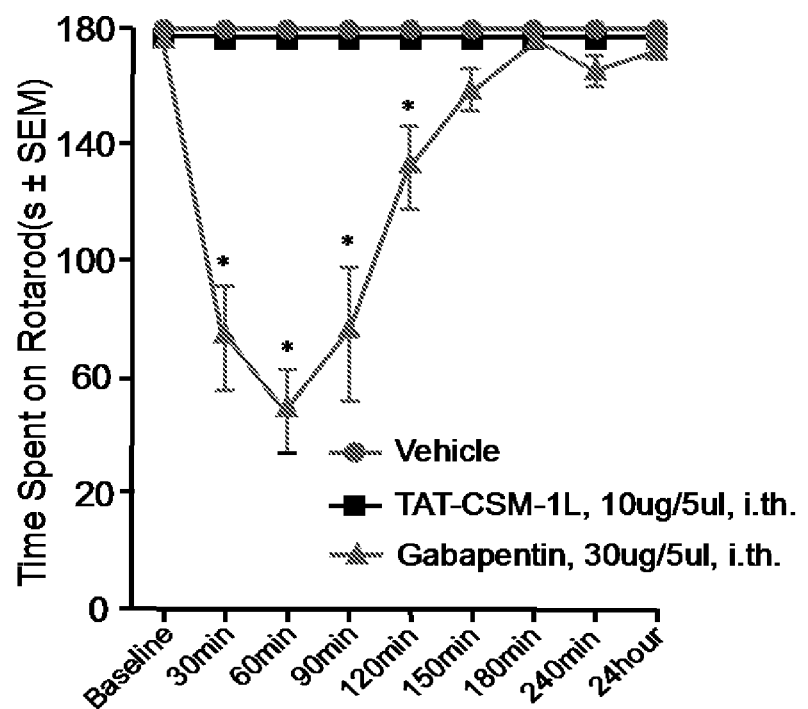
FIG. 9. Testing of motor impairment. Gabapentin resulted in significant sedation/motor impairment in rats whereas tat-CSM-1S did not result in any motor impairment/sedation over a 24 hour period. (*, $p<0.01$, n=6-8).

Efficacy of tat-CSM-1S peptide. In order to determine whether CRMP2 SUMOylation motif (CSM) peptides inhibit chronic pain the inventors tested tat-CSM-1S in a reliable long-lasting model of neuropathic pain after spinal delivery. The spared nerve injury model resulted in significant mechanical and thermal hypersensitivity (FIGS. 7A-7B, post-surgery group) on day 5 after injury. Spinal delivery (i.th.) of tat-CSM-1S at 10 μg/5 μl resulted in a significant long lasting reversal of both thermal and mechanical hypersensitivity (FIGS. 7A-7B) that returned to the injury baseline by 24 hrs. In comparison to clinically used drugs, morphine and gabapentin, the tat-CSM-1S resulted in higher potency, equivalent efficacy at the dose tested and had a significantly longer duration of action (FIGS. 8A-8B). No changes in latencies or thresholds were seen in sham control animals suggesting tat-CSM-1S does not alter non-injured latencies/thresholds (FIGS. 7A-7B). Because the current clinically used medications such as gabapentin result in severe sedation in humans, we determined whether our novel tat-CSM-1S would result in similar sedative or motor impairment (ruling out false positives in pain behavioral tests based on motor reflex is of major importance). Naïve male SD rats were used to determine sedation/motor impairment so that results are not influenced by "states of injury". The spinal delivery of tat-CSM-1S resulted in no motor impairment or sedation (FIG. 9) since all animals remained on the rotating rod until cut off (180 s). In contrast, gabapentin, a drug known to produce severe sedation in humans, resulted in a decrease in the ability of naïve rats to remain on the rotating rod (FIG. 9).

Determination of the mechanism of Action of CRMP2 SUMOylation-mediated effects on Nav1.7 trafficking. The SUMO motif in CRMP2 is 7 amino acids in length, centered on the SUMOylated lysine 374 of CRMP2. Removal of this motif results in a reduction in $Na^+$ current density via Nav1.7, but not Nav1.1 or Nav1.3, channels; the reduction in current density is commensurate with a reduction in cell surface expression of Nav1.7. The mechanism(s) by which this Nav1.7 reduction occurs is not known and is the focus of this aim. HEK293 cells stably expressing Nav1.7 are used, neuronal model CAD cells, and dorsal root ganglion (DRG) sensory neurons from male SD rats. As Nav1.8 is also expressed in DRG neurons express Nav1.7 and has also been linked to pain, we will also test effects of SUMOylation on Nav1.8. Plasmids expressing CRMP2 SUMO-null mutant and the novel tat-CSM-1S peptide will be used to dissect the relationship between SUMOylation and Nav1.7 trafficking. Protein phosphorylation may impact subsequent SUMOylation. Whether the same holds true for CRMP2 will be evaluated. Utilizing electrophysiology on cells expressing combined phosphorylation-SUMOylation null CRMP2 mutant plasmids, the investigators will investigate if the cross talk between these post-translational modifications together coordinates Nav1.7 trafficking. Proteomics analyses of cells expressing these constructs will be performed to determine if the interactome of the phosphorylation-SUMOylation null CRMP2 mutant is different from that of each single modification mutant alone.

The inventors have previously shown that genetic ablation of the SUMO motif in CRMP2 results in a reduction in Nav1.7 current density via a decrease in surface trafficking. Pharmacological manipulation of CRMP2 with the CRMP2 SUMOylation motif (CSM) "decoy" peptide also resulted in a similar decrement in Nav1.7 current in HEK293 cells expressing Nav1.7 (FIGS. 4A-4D).

The inventors' data using the Cdk5-site (S522A) phosphorylation null mutant and co-expression of the SUMOylation machinery implicates the importance of the phosphorylation-SUMOylation crosstalk in coordinating Nav1.7 trafficking (FIG. 5).

Assessment of CRMP2 SUMOylation motif peptides in models of acute and chronic pain The Nav1.7 channel is a molecular target for chronic pain research in which designing selective and specific antagonist that lack unwanted side effects have been unfruitful. Although Nav1.7 is found in the DRG and not the central nervous system and has been associated with debilitating chronic pain conditions such as erythromelalgia, paroxysmal extreme pain disorder and diabetic neuropathy, pharmaceutical companies and academia have not capitalized on this unique target for chronic pain. Nav1.7 is upregulated and promotes chronic pain in animal models of chronic peripheral inflammation and in peripheral nerve injury. Here, studies are designed to alter the level of expression of the Nav1.7 on the surface of the peripheral neurons under conditions of chronic inflammation and nerve injury using a small ubiquitin-like modification to alter CRMP2 that choreographs Nav1.7 trafficking. This mechanism has been shown to decrease trafficking of Nav1.7, but not other closely related sodium channels such as Nav1.1 or Nav1.3, channels. In addition, the studies provided herein have shown that a novel peptide (tat-CSM-1S) in this pathway significantly decreases both thermal and mechanical hypersensitivity after nerve injury while having no effect on motor activity or no obvious signs of impairment. Therefore, the pharmacology of novel disclosed compounds will be tested in vivo for: (a) anti-thermal and anti-mechanical hypersensitivity in a well accepted model of neuropathic pain (spared nerve injury—SNI) as well as a chronic model of inflammatory pain (Freund's Complete Adjuvant—CFA in the hindpaw); (b) dose- and time-response data will be collected; (c) comparison to currently available drugs used for neuropathic pain morphine and gabapentin; (d) dorsal root ganglia (DRGs) and spinal cords from uninjured and injured rats, treated with test compounds or vehicle, will be examined for their levels of Nav1.7 and CRMP2; (e) DRGs and spinal cord tissues will also be subject to proteomics-based analyses to identify alternative targets and/or biomarkers of injury; (f) sedation/motor effects using rotarod; and (g) addictive liability using condition placed preference (CPP). All studies will utilize male Sprague Dawley rats (Harlan, 175 to 225 g). All studies will be performed in a blinded fashion; drugs/vehicle will be given by the intrathecal route (tests at site of action) and by the intranasal route (systemic administration for BBB penetration). The respiratory tract, and the nose in particular, offers opportunities for improved drug delivery. Many drugs are rapidly and efficiently absorbed from the nasal cavity and, as a result, the nasal route may be used in crisis treatments (for example, for pain and nausea). Direct nose-brain delivery of peptides in sustained-release biodegradable nanoparticles is believed to be an effective mode of therapy for enhancing CNS bioavailability and a highly relevant route of delivery for military personnel in active duty combat situations.

Testing novel compounds after spinal administration in the SNI Model. Studies using the spared nerve injury model and behavioral testing of both mechanical and thermal hypersensitivity will be performed in the absence and presence of at least one, such as 2 disclosed compounds, vehicle and positive controls of clinically used drugs, morphine and gabapentin. Compounds will be administered by the spinal (intrathecal, i.th.) route to assure direct delivery to the site of synaptic connections between the periphery (site of damage) and the central nervous system. Studies will begin with animals undergoing i.th. catheter placement and a 5 day recovery. Animals that demonstrate normal behaviors will then undergo baseline mechanical and thermal testing (see General Methods) to determine latencies and thresholds, respectively. Next, rats will undergo either a spared nerve injury (SNI) or a sham surgery as control (see General Methods). Studies will include three groups of animals that undergo spinal nerve injury and receive i.th. doses of novel compounds (10 µg/5 ul and either increasing (30 µg/5 ul) or decreasing doses (3 µg/5 ul) based on a 1/3 log dose until a dose response curve is constructed; the second group will receive the vehicle used for the novel compounds (5 µl, i.th.); and the third group of animals will be divided and receive morphine (starting does 10 µg/5 ul) or gabapentin (starting dose 30 µg/5 ul) creating dose response curves for comparison. Groups will include nine animals based on previous analysis (detailed in Budget Justification section). Time points for behavioral measurements after drug administration include every 30 min out to 180 min, 240 min and 24 hr or until the return to post surgery (hypersensitive) state. In addition to testing in SNI, the same three groups (novel compounds, vehicle, positive controls) will be tested in sham surgery (exposure of sciatic nerves but no ligation) animals in the same manner.

Testing compounds after intranasal administration in the SNI Model. These studies will be performed as described above except with an intranasal route of administration as described. Based on previous studies on morphine as an intranasal drop, doses of 1 to 5 mg/kg in a total volume of 48 µl over time (i.e., 3 µl at a time of test compounds or controls, alternating the nostrils, with a lapse of 2 min between each administration, for a total of 16 times=total volume of 480) will be placed near the rat's naris and naturally inhaled into the nasal cavity. Dose- and time-response curves will be generated using known efficacy in comparison to morphine effects based on the ratios found after spinal administration studies described above. Studies will include at least one, such as 2 disclosed compounds, vehicle and positive controls (gabapentin and morphine) and all studies will be performed in a blinded fashion.

Testing compounds after spinal administration in the CFA Model. Complete Freund's Adjuvant (CFA) contains a *mycobacterium* that results in tissue damage and elicits a chronic inflammation resulting in thermal and mechanical hypersensitivity. Compounds will be administered by the i.th. route. Animals will undergo i.th. catheter placement and a 5 day recovery. Animals that demonstrate normal behaviors will then undergo baseline mechanical and thermal testing to determine latencies and thresholds, respectively. CFA (Sigma-Aldrich) will be administered intradermally by injection of 150 µl of CFA or Incomplete Freund's adjuvant (IFA; Sigma-Aldrich—lacks *mycobacterium* and therefore does not cause chronic inflammatory pain) as control groups, into the dorsal surface of the rat left hind paw (as before). Thermal and mechanical hyperalgesia tests will be conducted 5 days after CFA or IFA injection to determine chronic pain states. Studies will include three groups of animals that undergo CFA injection in the hindpaw and receive i.th. doses of novel compounds (based on SNI studies, 5 µl). A dose-response curve will be created, the second group will receive the vehicle used for the novel compounds (50) and the third group of animals will receive morphine (starting does 10 µg/5 µl) or gabapentin (starting dose 30 µg/5 µl) creating dose-response curves for comparison. Groups will include nine animal and time points for behavioral measurements after drug administration include every 30 min out to 180 min, 240 min and 24 hr or until the return to the post CFA (hypersensitive) state. In addition to testing in CFA treated animals, the same groups (novel compounds, vehicle, positive controls) will be tested in IFA-treated animals in the same manner and any significant changes in hindpaw thresholds or latencies will be recorded.

Testing compounds after intranasal administration in the CFA Model. These studies will be performed as described above except with an intranasal route of administration as described. Based on previous studies on morphine as an intranasal drop, doses of 1 to 5 mg/kg in a total volume of 48 µl over time (i.e., 3 µl at a time of test compounds or controls, alternating the nostrils, with a lapse of 2 min between each administration, for a total of 16 times=total volume of 48 µl) will be placed near the rat's naris and naturally inhaled into the nasal cavity. Dose- and time-response curves will be generated using known efficacy in comparison to morphine effects based on the ratios found after spinal administration studies. Studies will include 2 disclosed compounds, vehicle and positive controls (gabapentin and morphine) and all studies will be performed in a blinded fashion.

Testing compounds after intrathecal and intranasal administration for motor deficit and/or rewarding behaviors in naïve animals. Motor impairment and/or sedation will be tested in naïve male SD rats (in order to determine the effects of the novel compounds alone without interference from an injury state) using the rotarod test (see General Methods). For spinal administration, animals will undergo i.th. catheter implantation, recover for 5 days, trained to use the rotarod and latencies in remaining on the rotating rod recorded as baseline activity. In both spinal and nasal administration studies, animals will be administered an effective dose at 90% ($ED_{90}$) antihyperalgesic dose from previous studies, vehicle or an antihyperalgesic $ED_{90}$ dose of morphine or gabapentin and monitored for their ability to remain on the rotarod.

Rewarding behaviors will be tested in naïve male SD rats (in order to determine the effects of the novel compounds alone-no interference by an injury state) using a Conditioned Place Preference (CPP) paradigm (see General Methods for Aim 3). In both spinal and nasal administration studies, animals will be administered an $ED_{90}$ antihyperalgesic dose from previous studies, vehicle or an antihyperalgesic $ED_{90}$ dose of morphine or gabapentin and monitored to determine if the compounds result in a positive CPP.

The data with a single dose of tat-CSM-1S significantly inhibits chronic pain after spinal administration without producing motor impairment (FIGS. 7A-7B, and FIG. 9). Based on these exciting data a dose-response curve of the disclosed novel compounds will be generated compared to the potency and efficacy to both gabapentin and morphine. If there is severe tissue necrosis due to CFA and/or a lack of an analgesic effect using the novel compounds, alternative models of acute and chronic inflammatory pain can be investigated including formalin flinch or carrageenan with comparison to a clinically used NSAID such as naproxen.

Previous studies with peptidic molecules such as oxytocin have demonstrated good bioavailability and access to the CNS by intranasal administration. Morphine has been given by the intranasal route and demonstrates analgesic efficacy in a rat model. An alternative route of administration to determine whether these novel compounds are active is to administer the disclosed compounds by the i.v. route and determine efficacy in the spared nerve injury model. Yet, another alternative method of delivery of peptides is the use of a viral vector similar to a recent publication by the Hogan group. These studies utilized an adeno-associated viral (AAV) vector, with a sequence encompassing a peptide from CRMP2 to disrupt the CRMP2-calcium channel interaction, for delivery directly to the DRGs which resulted in significant anti-nociceptive activity in the spared nerve injury model. It is believed that the disclosed compounds would not result in any rewarding behavior or become an abused substance since they are non-narcotic and do not retain a mechanism that would enhance dopamine release.

Example 3

Methods of Decreasing Nociception

This example describes methods of decreasing nociception, such as in a subject at risk or has acute pain, chronic pain, nociceptic pain, cancer pain, neuralgia pain, myalgia pain, burn pain, arthritic pain, bowel inflammation pain, bone and/or osteoporosis pain, inflammatory pain or a combination thereof. In some examples, the subject is at risk or has a neurological disorder, such as Parkinson's Disease, Alzheimer's Disease, Pick's Disease, and/or Chronic Fatigue Syndrome. In some examples, the subject is at risk or has an emotional and/or mood disorder, such as depression, PTSD, anxiety, addiction and obsessive compulsive disorder.

Based upon the teachings herein, methods of decreasing nociception are provided. In some embodiments, the methods comprise administering to a subject an effective amount of a disclosed isolated polypeptide or composition, thereby decreasing nociception in the subject. In one particular example, a subject in need of treatment is identified. A composition comprising a CSM-1 peptide conjugated to a cell penetrating motif is then administered to the subject orally at a concentration of 200-600 mg every day up to the study termination. At 14-day intervals, subjects will be assessed. An at least 10% decrease in one or more signs or symptoms will identify the treatment as useful for decreasing nociception.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An isolated polypeptide consisting of
three to twenty amino acids capable of inhibiting collapsin response mediator protein 2(CRMP2)- small ubiquitin-like modifier (SUMO)ylation mediated trafficking of voltage gated sodium channel 1.7(Nav1.7) function and wherein the three to twenty amino acids comprise the amino acid sequence KMD, wherein the peptide comprises the amino acid sequence GKMDENQ (SEQ ID NO: 1; CSM-1S) or wherein the peptide comprises the amino acid sequence WDKAVVTGKMDENQFVAV (SEQ ID NO: 2; CSM-1L), and a cell penetrating motif having an amino acid sequence selected from the following:

(SEQ ID NO: 3)
(a) GRKKRRQRRRPPQ;

(SEQ ID NO: 4)
(b) RQIKIWFQNRRMKWKK;

(SEQ ID NO: 5)
(c) LLIILRRRIRKQAHAHSK;

(SEQ ID NO: 6)
(d) RGGRLSYSRRRFSTSTGR;

(SEQ ID NO: 7)
(e) RRRRRRRR;

-continued (f) GRRRRRRRRPPQ; (SEQ ID NO: 8)

(g) AAVALLPAVLLALLAP; (SEQ ID NO: 9)

(H) KLALKLALKALKAALKLA; (SEQ ID NO: 10)

(i) TRRQRTRRARRNR; (SEQ ID NO: 11)

(j) PLSSIFSRIGDP; (SEQ ID NO: 12)

(k) MALNLGWLLALFVTMWTDVGLCKKRPKP; (SEQ ID NO: 13)

(l) AGYLLGKINLKALAALAKKIL; (SEQ ID NO: 14)
or (m) PLSSIFSRIGDP. (SEQ ID NO: 15)

2. A composition comprising the isolated polypeptide of claim 1 and a pharmaceutically acceptable carrier.

3. A method of decreasing nociception, comprising administering to a subject in need thereof an effective amount of the isolated polypeptide of claim 1, thereby decreasing nociception in the subject.

4. The method of claim 3, wherein administering comprises intravenous, intrathecal, intraperitoneal, subcutaneous, oral, transdermal, epidural, or sublingual administration.

5. The method of claim 3, wherein the subject has acute pain, chronic pain, nociceptic pain, cancer pain, neuralgia pain, myalgia pain, burn pain, arthritic pain, bowel inflammation pain, bone and/or osteoporosis pain, inflammatory pain or a combination thereof.

6. The method of claim 3, wherein the subject has a neurological disorder, such as Parkinson's Disease, Alzheimer's Disease, Pick's Disease, and/or Chronic Fatigue Syndrome.

7. The method of claim 3, wherein the subject has an emotional and/or mood disorder, such as depression, post-traumatic stress disorder (PTSD), anxiety, addiction and obsessive compulsive disorder.

8. A method for inhibiting voltage gated sodium channel 1.7(Nav1.7) activity, comprising contacting a cell with an effective amount of the isolated polypeptide of claim 1, thereby inhibiting voltage gated sodium channel 1.7 (Nav1.7) activity.

9. The method of claim 8, wherein inhibiting Nav1.7 activity comprises inhibiting and/or reducing collapsin response mediator protein 2(CRMP2)- small ubiquitin-like modifier (SUMO)ylation mediated trafficking of voltage gated sodium channel 1.7(Nav1.7) function as compared to that occurring in an untreated cell.

10. The method of claim 8, wherein the cell is in a mammal.

* * * * *